(12) United States Patent
Whitfield et al.

(10) Patent No.: US 11,918,231 B2
(45) Date of Patent: *Mar. 5, 2024

(54) ARTICULATING ENDOSCOPIC SURGICAL CLIP APPLIER

(71) Applicant: Covidien LP, Mansfield, MA (US)

(72) Inventors: Kenneth H. Whitfield, North Haven, CT (US); Csaba L. Rethy, Westport, CT (US)

(73) Assignee: COVIDIEN LP, Mansfield, MA (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/544,023

(22) Filed: Dec. 7, 2021

(65) Prior Publication Data

US 2022/0096091 A1 Mar. 31, 2022

Related U.S. Application Data

(63) Continuation of application No. 16/299,356, filed on Mar. 12, 2019, now Pat. No. 11,213,299, which is a
(Continued)

(51) Int. Cl.
*A61B 17/128* (2006.01)
*A61B 17/068* (2006.01)
(Continued)

(52) U.S. Cl.
CPC ........ *A61B 17/1285* (2013.01); *A61B 17/068* (2013.01); *A61B 17/083* (2013.01);
(Continued)

(58) Field of Classification Search
CPC .............. A61B 17/068; A61B 17/0682; A61B 17/07207; A61B 17/128; A61B 17/1285;
(Continued)

(56) References Cited

U.S. PATENT DOCUMENTS

| 3,363,628 A | 1/1968 | Wood |
| 3,638,847 A | 2/1972 | Noiles et al. |

(Continued)

FOREIGN PATENT DOCUMENTS

| AU | 2013254887 A1 | 11/2013 |
| CA | 1163889 A | 3/1984 |

(Continued)

OTHER PUBLICATIONS

Extended European Search Report corresponding to Patent Application EP 19151805.9 dated Sep. 5, 2019.

(Continued)

*Primary Examiner* — Todd J Scherbel
(74) *Attorney, Agent, or Firm* — Carter, DeLuca & Farrell, LLP

(57) ABSTRACT

An apparatus for application of surgical clips to body tissue is provided and includes a handle assembly and a shaft assembly. The handle assembly includes a drive assembly; and a trigger operatively connected to the drive assembly. The shaft assembly extends from the handle assembly and includes an articulating neck assembly; and an end effector assembly supported on a distal end of the articulating neck assembly and being configured to form a surgical clip in place on the body tissue.

20 Claims, 41 Drawing Sheets

Related U.S. Application Data continuation of application No. 15/151,535, filed on May 11, 2016, now Pat. No. 10,271,854, which is a continuation of application No. 14/486,306, filed on Sep. 15, 2014, now Pat. No. 9,393,024, which is a continuation of application No. 13/772,998, filed on Feb. 21, 2013, now Pat. No. 8,845,659, which is a continuation of application No. 13/004,064, filed on Jan. 11, 2011, now Pat. No. 8,403,945.

(60) Provisional application No. 61/308,093, filed on Feb. 25, 2010.

(51) Int. Cl.
*A61B 17/08* (2006.01)
*A61B 17/10* (2006.01)
*A61B 17/122* (2006.01)
*A61B 17/00* (2006.01)
*A61B 17/29* (2006.01)

(52) U.S. Cl.
CPC ........ *A61B 17/105* (2013.01); *A61B 17/1222* (2013.01); *A61B 2017/003* (2013.01); *A61B 2017/00309* (2013.01); *A61B 2017/00314* (2013.01); *A61B 2017/00318* (2013.01); *A61B 2017/00323* (2013.01); *A61B 2017/00407* (2013.01); *A61B 2017/2908* (2013.01); *A61B 2017/2923* (2013.01)

(58) Field of Classification Search
CPC ........ A61B 2017/29; A61B 2017/2908; A61B 2017/2919; A61B 2017/2922; A61B 2017/2923; A61B 2017/2926; A61B 2017/2927; A61B 2017/2929; A61B 2017/2932; A61B 2017/2933; A61B 2017/2934; A61B 2017/2937; A61B 2017/23947

See application file for complete search history.

(56) References Cited

U.S. PATENT DOCUMENTS

| | | |
|---|---|---|
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |

(56) References Cited

U.S. PATENT DOCUMENTS

| | | |
|---|---|---|
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,259,366 A | 11/1993 | Reydel et al. |
| 5,269,792 A | 12/1993 | Kovac et al. |
| 5,281,228 A | 1/1994 | Wolfson |
| 5,282,807 A | 2/1994 | Knopfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,582,616 A | 12/1996 | Bolduc et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |

(56) References Cited

U.S. PATENT DOCUMENTS

| | | |
|---|---|---|
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | Mckean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B2 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |

(56) References Cited

U.S. PATENT DOCUMENTS

| | | |
|---|---|---|
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 * | 3/2013 | Whitfield ............ A61B 17/105 606/143 |
| 8,403,946 B2 | 3/2013 | Whitfield et al. |
| 8,408,442 B2 | 4/2013 | Racenet et al. |

(56) References Cited

U.S. PATENT DOCUMENTS

| | | |
|---|---|---|
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 * | 9/2014 | Whitfield ............ A61B 17/105 606/143 |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 * | 7/2016 | Whitfield ............ A61B 17/083 |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,271,854 B2 | 4/2019 | Whitfield et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |

(56) References Cited

U.S. PATENT DOCUMENTS

| | | |
|---|---|---|
| 10,426,489 B2 | 10/2019 | Baril |
| 10,470,765 B2 | 11/2019 | Malkowski |
| 10,485,538 B2 | 11/2019 | Whitfield et al. |
| 10,492,795 B2 | 12/2019 | Williams |
| 10,537,329 B2 | 1/2020 | Malkowski |
| 10,542,999 B2 | 1/2020 | Zergiebel |
| 10,548,602 B2 | 2/2020 | Baril et al. |
| 10,568,635 B2 | 2/2020 | Whitfield et al. |
| 10,582,931 B2 | 3/2020 | Mujawar |
| 10,603,038 B2 | 3/2020 | Mujawar et al. |
| 10,610,236 B2 | 4/2020 | Baril |
| 10,639,032 B2 | 5/2020 | Baril et al. |
| 10,639,044 B2 | 5/2020 | Prior |
| 10,653,429 B2 | 5/2020 | Baril et al. |
| 10,660,639 B2 | 5/2020 | Hartoumbekis |
| 10,660,651 B2 | 5/2020 | Baril et al. |
| 10,660,652 B2 | 5/2020 | Tan et al. |
| 10,660,723 B2 | 5/2020 | Baril |
| 10,660,725 B2 | 5/2020 | Baril et al. |
| 10,675,043 B2 | 6/2020 | P V R |
| 10,675,112 B2 | 6/2020 | Baril et al. |
| 10,682,135 B2 | 6/2020 | Sorrentino et al. |
| 10,682,146 B2 | 6/2020 | Rockrohr et al. |
| 10,702,278 B2 | 7/2020 | Tokarz et al. |
| 10,702,279 B2 | 7/2020 | Xu et al. |
| 10,702,280 B2 | 7/2020 | Cai et al. |
| 10,709,455 B2 | 7/2020 | Baril et al. |
| 10,722,235 B2 | 7/2020 | Baril et al. |
| 10,722,236 B2 | 7/2020 | Zammataro |
| 10,743,851 B2 | 8/2020 | Swayze et al. |
| 10,743,886 B2 | 8/2020 | Malkowski et al. |
| 10,743,887 B2 | 8/2020 | P V R |
| 10,758,234 B2 | 9/2020 | Malkowski et al. |
| 10,758,244 B2 | 9/2020 | Williams |
| 10,758,245 B2 | 9/2020 | Baril et al. |
| 10,765,431 B2 | 9/2020 | Hu et al. |
| 10,765,435 B2 | 9/2020 | Gokharu |
| 10,786,262 B2 | 9/2020 | Baril et al. |
| 10,786,263 B2 | 9/2020 | Baril et al. |
| 10,786,273 B2 | 9/2020 | Baril et al. |
| 10,806,463 B2 | 10/2020 | Hartoumbekis |
| 10,806,464 B2 | 10/2020 | Raikar et al. |
| 10,828,036 B2 | 11/2020 | Baril et al. |
| 10,835,260 B2 | 11/2020 | Baril et al. |
| 10,835,341 B2 | 11/2020 | Baril et al. |
| 10,849,630 B2 | 12/2020 | P V R |
| 10,863,992 B2 | 12/2020 | Czernik et al. |
| 10,932,791 B2 | 3/2021 | P V R |
| 10,932,793 B2 | 3/2021 | Yi et al. |
| 10,945,734 B2 | 3/2021 | Baril et al. |
| 10,959,737 B2 | 3/2021 | P V R |
| 10,993,721 B2 | 5/2021 | Baril et al. |
| 11,026,696 B2 | 6/2021 | Zammataro |
| 11,033,256 B2 | 6/2021 | Zammataro et al. |
| 11,051,827 B2 | 7/2021 | Baril et al. |
| 11,051,828 B2 | 7/2021 | Baril et al. |
| 11,058,432 B2 | 7/2021 | Bhatnagar et al. |
| 11,071,553 B2 | 7/2021 | Raikar et al. |
| 11,116,513 B2 | 9/2021 | Dinino et al. |
| 11,116,514 B2 | 9/2021 | Yue et al. |
| 11,134,956 B2 | 10/2021 | Shankarsetty |
| 11,147,566 B2 | 10/2021 | Pilletere et al. |
| 11,213,298 B2 | 1/2022 | Sorrentino et al. |
| 11,213,299 B2 | 1/2022 | Whitfield et al. |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0230198 A1 | 11/2004 | Manzi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0234478 A1 | 10/2005 | Wixey et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |

(56) References Cited

U.S. PATENT DOCUMENTS

| | | |
|---|---|---|
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0057102 A1 | 3/2010 | Sorrentino et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0028994 A1 | 2/2011 | Whitfield et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0101066 A1 | 5/2011 | Farascioni et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029534 A1 | 2/2012 | Whitfield |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0234894 A1 | 9/2012 | Kostrzewski |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Arson et al. |
| 2014/0005678 A1 | 1/2014 | Shelton, IV et al. |
| 2014/0074143 A1 | 3/2014 | Fitzgerald et al. |
| 2014/0131421 A1 | 5/2014 | Viola |
| 2014/0188159 A1 | 7/2014 | Steege |
| 2014/0252065 A1 | 9/2014 | Hessler et al. |
| 2014/0263565 A1 | 9/2014 | Lytle, IV et al. |
| 2014/0276970 A1 | 9/2014 | Messerly et al. |
| 2014/0309677 A1 | 10/2014 | Baldwin |
| 2014/0324074 A1 | 10/2014 | Crainich et al. |
| 2014/0371728 A1 | 12/2014 | Vaughn |
| 2015/0032131 A1 | 1/2015 | Sorrentino et al. |
| 2015/0190133 A1 | 7/2015 | Penna et al. |
| 2015/0196298 A1 | 7/2015 | Menn et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2015/0327879 A1 | 11/2015 | Garrison et al. |
| 2016/0000428 A1 | 1/2016 | Scirica |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0166255 A1 | 6/2016 | Fischvogt |
| 2016/0192927 A1 | 7/2016 | Kostrzewski |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0249927 A1 | 9/2016 | Beckman et al. |
| 2016/0256157 A1 | 9/2016 | Rockrohr et al. |
| 2016/0256158 A1 | 9/2016 | Whitfield et al. |
| 2016/0296232 A1 | 10/2016 | Campbell |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0165015 A1 | 6/2017 | Hess et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133590 A1 | 5/2019 | Richard |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0159782 A1 | 5/2019 | Kamaraj et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |

(56) References Cited

U.S. PATENT DOCUMENTS

| | | |
|---|---|---|
| 2019/0209177 A1 | 7/2019 | Whitfield et al. |
| 2019/0216464 A1 | 7/2019 | Baril et al. |
| 2019/0239893 A1 | 8/2019 | Shankarsetty |
| 2019/0298377 A1 | 10/2019 | Castro |
| 2019/0321048 A1 | 10/2019 | Dinino et al. |
| 2019/0328391 A1 | 10/2019 | Holsten et al. |
| 2019/0328399 A1 | 10/2019 | Baril et al. |
| 2020/0008806 A1 | 1/2020 | Dinino et al. |
| 2020/0046329 A1 | 2/2020 | Baril et al. |
| 2020/0046359 A1 | 2/2020 | Thomas et al. |
| 2020/0046363 A1 | 2/2020 | Baril et al. |
| 2020/0046365 A1 | 2/2020 | Baril et al. |
| 2020/0046443 A1 | 2/2020 | Baril et al. |
| 2020/0060686 A1 | 2/2020 | Williams |
| 2020/0113569 A1 | 4/2020 | Zergiebel |
| 2020/0129183 A1 | 4/2020 | Baril et al. |
| 2020/0146687 A1 | 5/2020 | Whitfield et al. |
| 2020/0170646 A1 | 6/2020 | Mujawar |
| 2020/0229825 A1 | 7/2020 | P V R |
| 2020/0261095 A1 | 8/2020 | Yi et al. |
| 2020/0315629 A1 | 10/2020 | Xu et al. |
| 2021/0059681 A1 | 3/2021 | Zhang et al. |
| 2021/0169482 A1 | 6/2021 | Baril et al. |
| 2021/0204946 A1 | 7/2021 | Banerjee et al. |
| 2021/0298758 A1 | 9/2021 | Thomas et al. |
| 2021/0401438 A1 | 12/2021 | Pilletere et al. |

FOREIGN PATENT DOCUMENTS

| | | |
|---|---|---|
| CN | 101164502 A | 4/2008 |
| CN | 202699217 U | 1/2013 |
| CN | 104605911 B | 2/2017 |
| DE | 29520789 U1 | 6/1996 |
| DE | 202005001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0576835 A2 | 1/1994 |
| EP | 0732078 A2 | 9/1996 |
| EP | 1769757 A1 | 4/2007 |
| EP | 3132756 A1 | 2/2017 |
| EP | 3476331 A1 | 5/2019 |
| GB | 2073022 A | 10/1981 |
| IN | 103251441 A | 8/2013 |
| JP | 06054858 | 3/1994 |
| JP | 2003033361 A | 2/2003 |
| JP | 2006154230 A | 6/2006 |
| JP | 2006277221 A | 10/2006 |
| JP | 2008017876 A | 1/2008 |
| JP | 2008200190 A | 9/2008 |
| JP | 2011186812 A | 9/2011 |
| JP | 2013166982 A | 8/2013 |
| WO | 9003763 A1 | 4/1990 |
| WO | 9624294 A1 | 8/1996 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |
| WO | 2018035796 A1 | 3/2018 |

OTHER PUBLICATIONS

Japanese Office Action corresponding to Patent Application JP 2018-537512 dated Sep. 9, 2019.
Extended European Search Report corresponding to Patent Application EP 19170951.8 dated Sep. 26, 2019.
Extended European Search Report corresponding to Patent Application EP 15908020.9 dated Oct. 9, 2019.
Japanese Office Action corresponding to Patent Application JP 2018-534822 dated Oct. 17, 2019.
Extended European Search Report corresponding to Patent Application EP 16884297.9 dated Oct. 31, 2019.
Extended European Search Report corresponding to Patent Application EP 16885490.9 dated Nov. 12, 2019.
Extended European Search Report corresponding to Patent Application EP 19191203.9 dated Dec. 9, 2019.
Extended European Search Report corresponding to Patent Application EP 19191226.0 dated Dec. 10, 2019.
Extended European Search Report corresponding to Patent Application EP 19172130.7 dated Dec. 19, 2019.
European Office Action corresponding to Patent Application EP 18 187 690.5 dated Mar. 23, 2020.
Extended European Search Report corresponding to Patent Application EP 16912243.9 dated Mar. 25, 2020.
Chinese First Office Action corresponding to Patent Application CN 201610694951.2 dated Apr. 23, 2020.
Partial Supplementary European Search Report corresponding to Patent Application EP 18899075.8 dated Jul. 1, 2021.
Australian Examination Report No. 1 corresponding to Patent Application AU 2015413639 dated Jul. 23, 2020.
Chinese First Office Action corresponding to Patent Application CN 201680078525.4 dated Jul. 28, 2020.
Japanese Office Action corresponding to Patent Application JP 2016-217970 dated Sep. 28, 2020.
Extended European Search Report corresponding to Patent Application EP 17895153.9 dated Dec. 17, 2020.
Extended European Search Report corresponding to Patent Application EP 20215391.2 dated Apr. 30, 2021.
Extended European Search Report corresponding to Patent Application EP 18873112.9 dated Oct. 18, 2021.
Extended European Search Report corresponding to Patent Application EP 21164196.4 dated Dec. 17, 2021.
Canadian Office Action dated Sep. 6, 2016 corresponding to Patent Application CA 2,728,538.
Japanese Office Action dated Sep. 1, 2014 corresponding to counterpart Patent Application JP 2011-039024.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.

(56) References Cited

OTHER PUBLICATIONS

Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.

(56) References Cited

OTHER PUBLICATIONS

European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
International Search Report and Written Opinion corresponding to International Application No. PCT/US18/050316 dated Dec. 31, 2018.
International Search Report and Written Opinion corresponding to International Application No. PCT/US18/050325 dated Jan. 7, 2019.
International Search Report and Written Opinion corresponding to International Application No. PCT/US2018/057922 dated Feb. 22, 2019.
Chinese First Office Action corresponding to Patent Application CN 201610055870.8 dated Aug. 1, 2019.
Japanese Office Action corresponding to Patent Application JP 2015-203499 dated Aug. 16, 2019.
Chinese Second Office Action corresponding to Patent Application CN 201510696298.9 dated Aug. 21, 2019.
Japanese Office Action corresponding to Patent Application JP 2018-516433 dated Aug. 21, 2019.
Chinese First Office Action corresponding to Patent Application CN 201580072284.8 dated Aug. 29, 2019.
Chinese First Office Action corresponding to Patent Application CN 201580073962.2 dated Sep. 5, 2019.
Extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
International Search Report corresponding to International Application No. PCT-US08-59859, completed Sep. 14, 2008; dated Sep. 18, 2008; (2 Pages).
Extended European Search Report corresponding to European Application No. EP 07 25 3807.7, completed Nov. 7, 2008; dated Nov. 26, 2008; (11 Pages).
Extended European Search Report corresponding to European Application No. EP 09 25 2049.3, completed Dec. 11, 2009; dated Jan. 12, 2010; (3 Pages).
Extended European Search Report corresponding to European Application No. EP 09 25 2050.1, completed Dec. 23, 2009; dated Jan. 21, 2010; (3 Pages).
Extended European Search Report corresponding to European Application No. EP 09 25 2051.9, completed Dec. 21, 2009; dated Jan. 28, 2010; (3 Pages).
Extended European Search Report corresponding to European Application No. EP 09 25 2052.7, completed Nov. 16, 2009; dated Nov. 24, 2009; (3 Pages).
Extended European Search Report corresponding to European Application No. EP 09 25 2053.5, completed Nov. 24, 2009; dated Dec. 1, 2009; (3 Pages).
Extended European Search Report corresponding to European Application No. EP 09 25 2054.3, completed Jan. 7, 2010; dated Jan. 22, 2010; (3 Pages).
Extended European Search Report corresponding to European Application No. EP 09 25 2056.8, completed Jan. 8, 2010; dated Feb. 5, 2010; (3 Pages).
Extended European Search Report corresponding to European Application No. EP 10 25 0497.4, completed May 4, 2010; dated May 12, 2010; (6 Pages).
Extended European Search Report corresponding to European Application No. EP 10 25 2079.8, completed Mar. 8, 2011; dated Mar. 17, 2011; (3 Pages).

European Search Report corresponding to European Application No. EP 05 81 0218.7, completed Apr. 18, 2011; dated May 20, 2011; (3 pages).
European Search Report corresponding to European Application No. EP 05 80 7612.6, completed May 2, 2011; dated May 20, 2011; (3 pages).
Extended European Search Report corresponding to European Application No. EP 10 25 1737.2, completed May 9, 2011; dated May 20, 2011; (4 pages).
Extended European Search Report corresponding to European Application No. EP 11 25 0214.1, completed May 25, 2011; dated Jun. 1, 2011; (3 Pages).
Extended European Search Report corresponding to European Application No. EP 11 00 2681.2, completed May 31, 2011; dated Jun. 10, 2011; (3 Pages).
European Search Report corresponding to European Application No. EP 05 80 2686.5, completed Jan. 9, 2012; dated Jan. 18, 2012; (3 Pages).
Extended European Search Report corresponding to European Application No. EP 12 15 1313.9, completed Mar. 20, 2012 and dated Apr. 12, 2012; (5 Pages).
Extended European Search Report corresponding to European Application No. EP 12 16 1291.5, completed Apr. 24, 2012 and dated May 4, 2012; (5 Pages).
Extended European Search Report corresponding to European Application No. EP 12 16 5891.8, completed Jun. 12, 2012 and dated Jun. 20, 2012; (6 Pages).
Extended European Search Report corresponding to European Application No. EP 12 16 2288.0, completed Jun. 4, 2012 and dated Jul. 7, 2012; (6 Pages).
Extended European Search Report corresponding to European Application No. EP 12 16 4955.2, completed Aug. 23, 2012 and dated Sep. 4, 2012; (5 Pages).
Extended European Search Report corresponding to European Application No. EP 11 25 0754.6, completed Oct. 22, 2012 and dated Oct. 31, 2012; (6 Pages).
Extended European Search Report corresponding to European Application No. EP 12 18 6401.1, completed Nov. 22, 2012 and dated Nov. 30, 2012; (7 Pages).
Extended European Search Report corresponding to European Application No. EP 12 18 6448.2, completed Nov. 28, 2012 and dated Dec. 10, 2012; (6 Pages).
Extended European Search Report corresponding to European Application No. EP 12 19 1706.6, completed Dec. 19, 2012 and dated Jan. 8, 2013; (6 Pages).
Extended European Search Report corresponding to EP 12 19 8745.7, completed Mar. 19, 2013 and dated Apr. 11, 2013; (8 Pages).
Extended European Search Report corresponding to EP 12 15 2989.5, completed Apr. 9, 2013 and dated Apr. 18, 2013; (9 Pages).
Extended European Search Report corresponding to EP 08 73 2820.9, completed Jul. 2, 2013 and dated Jul. 9, 2013; (10 Pages).
Extended European Search Report corresponding to EP 13 17 2008.8, completed Aug. 14, 2013 and dated Aug. 28, 2013; (8 Pages).
Extended European Search Report corresponding to EP 13 16 6382.5, completed Nov. 19, 2013 and dated Nov. 28, 2013; (8 Pages).
Extended European Search Report corresponding to EP 11 25 0194.5, completed Nov. 25, 2013 and dated Dec. 3, 2013; (8 Pages).
Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.

(56) References Cited

OTHER PUBLICATIONS

Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

\* cited by examiner

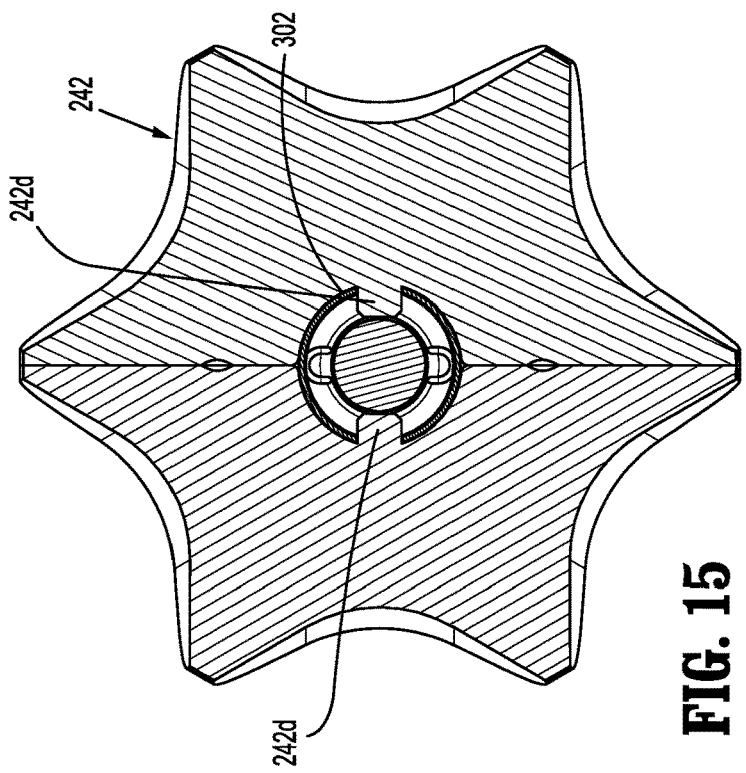
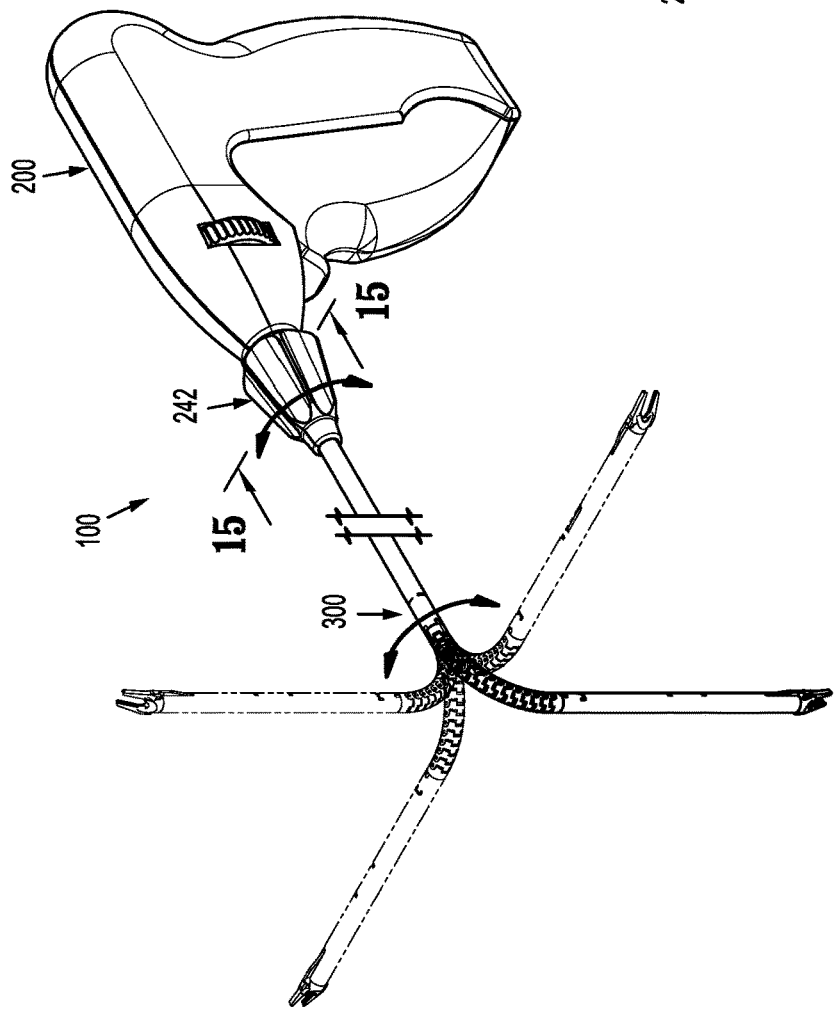
FIG. 15
FIG. 14

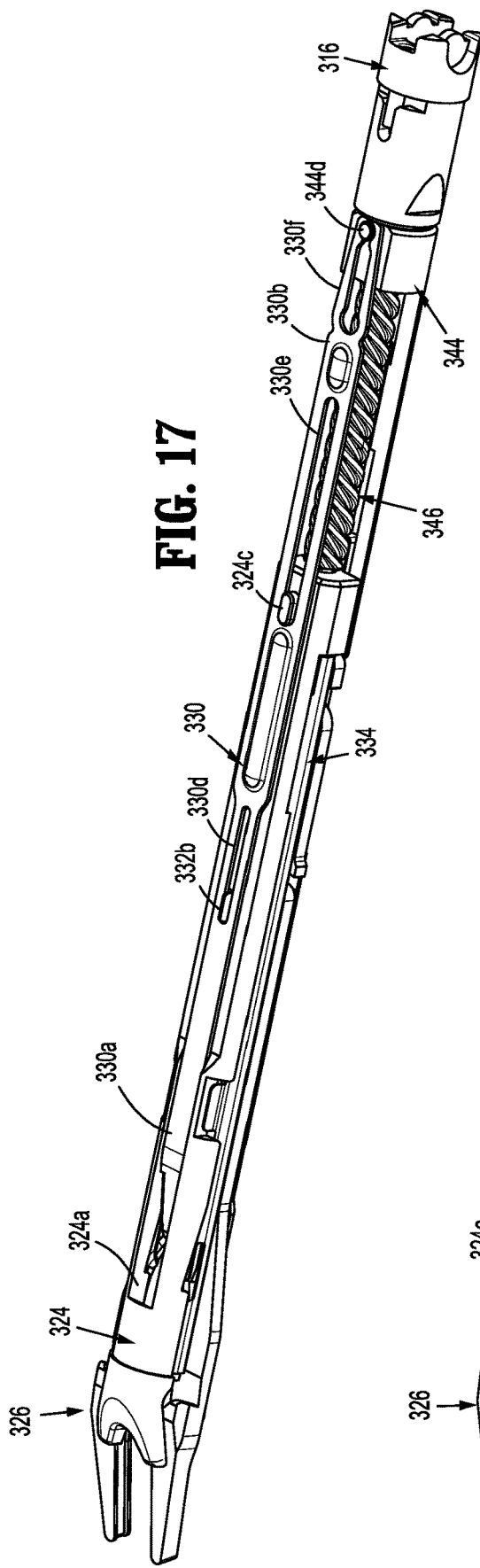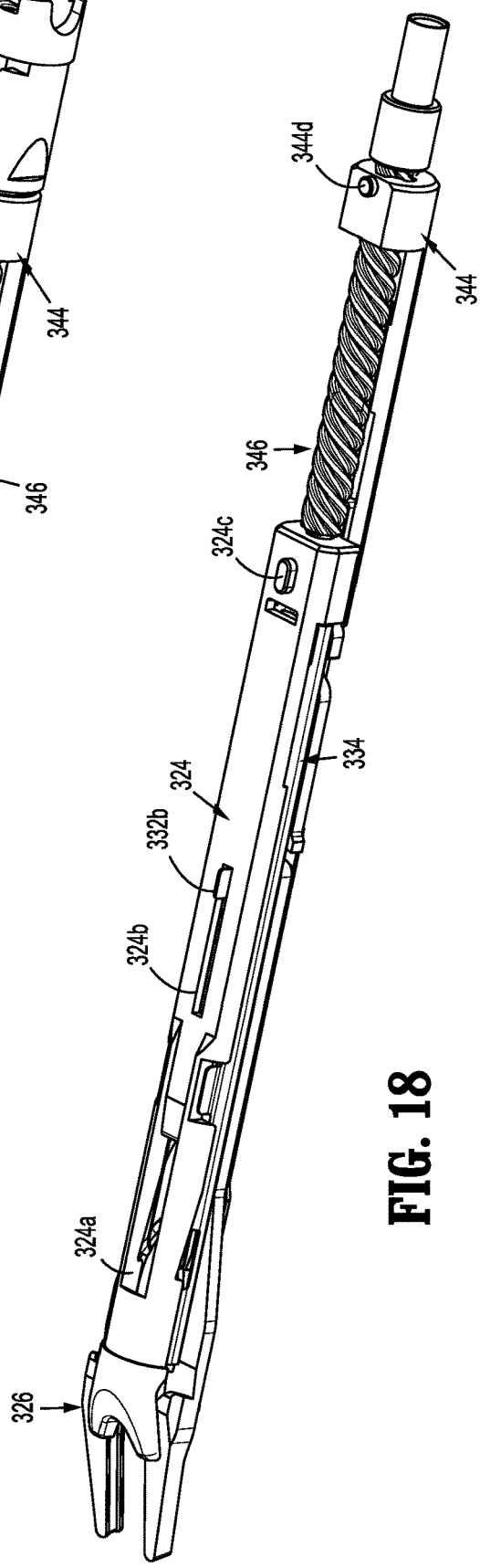

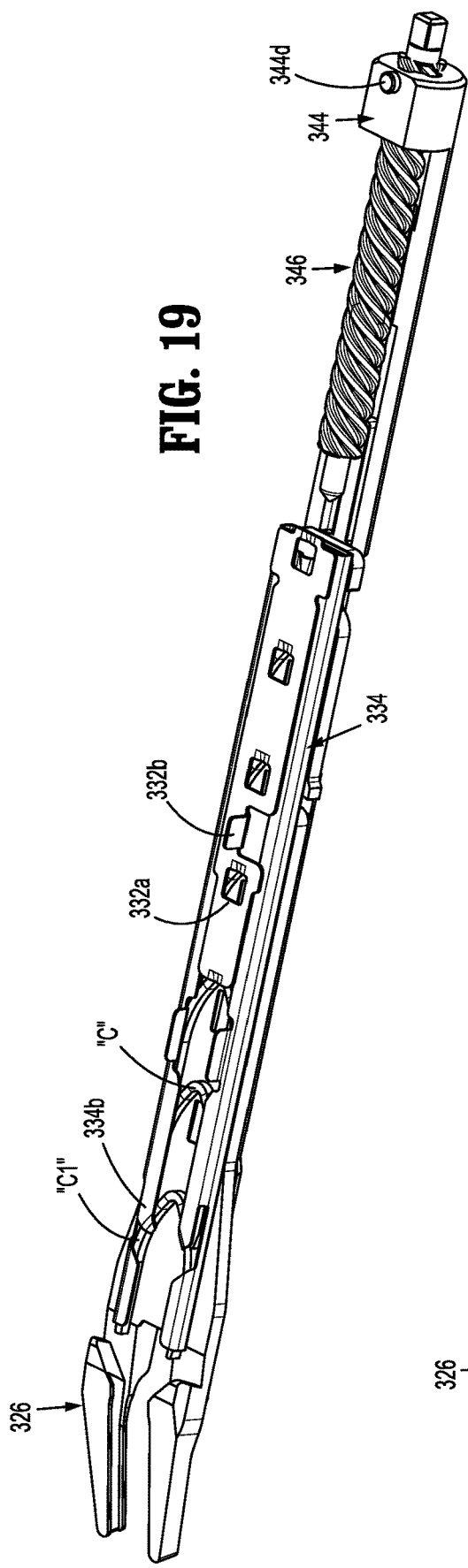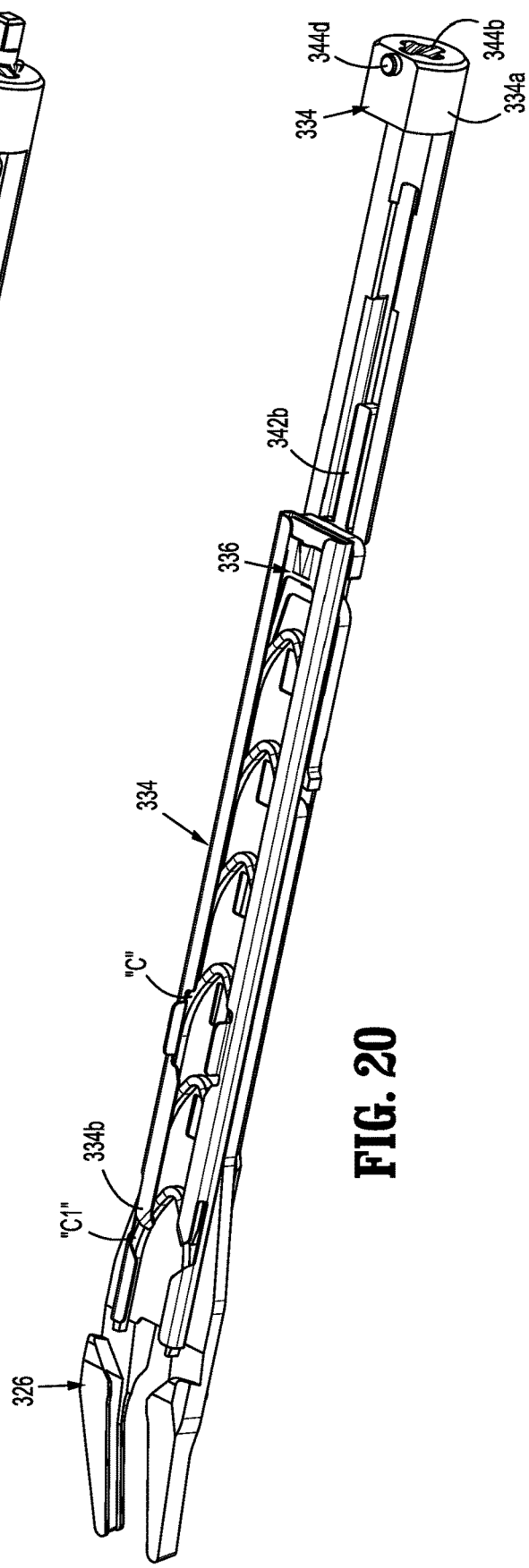

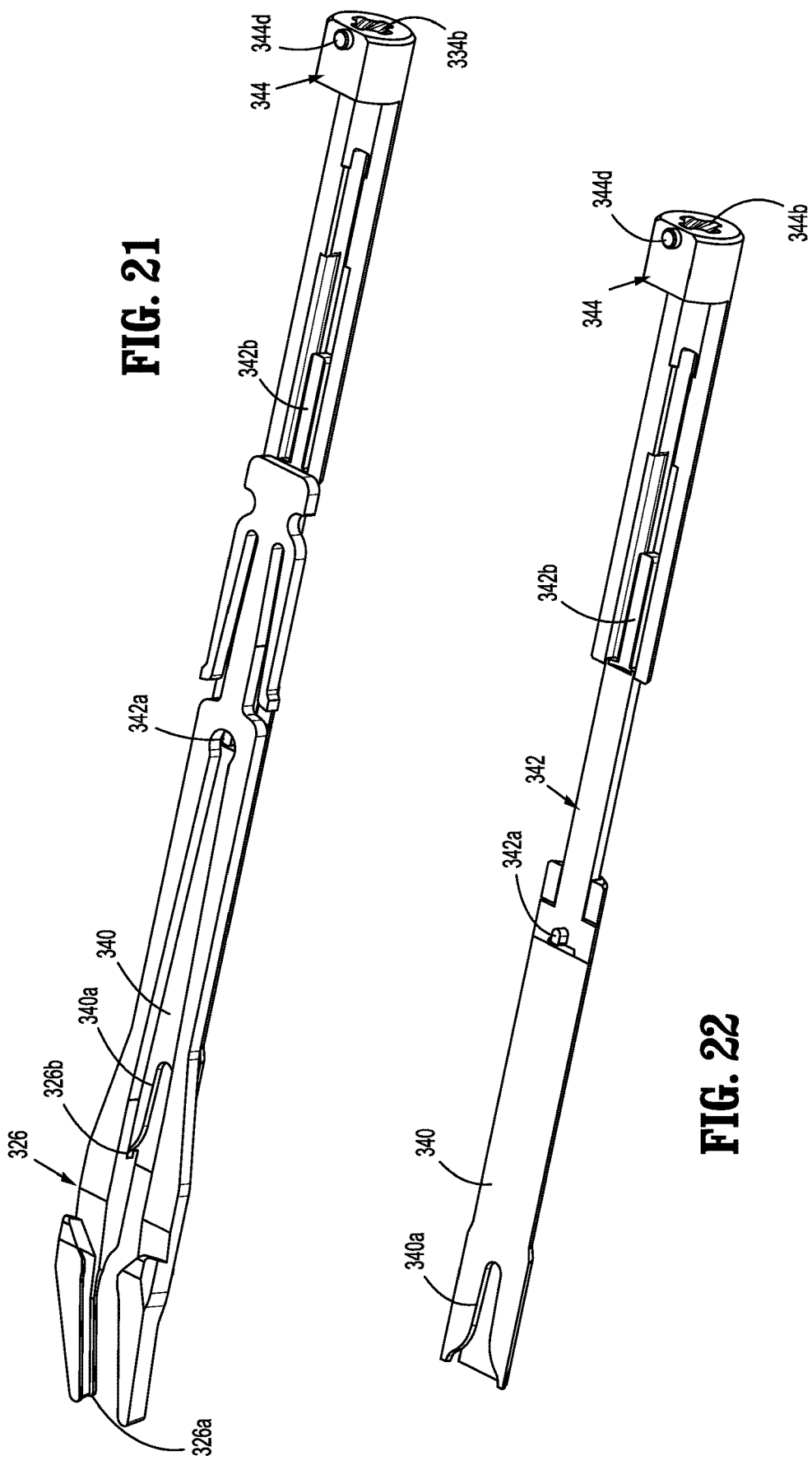

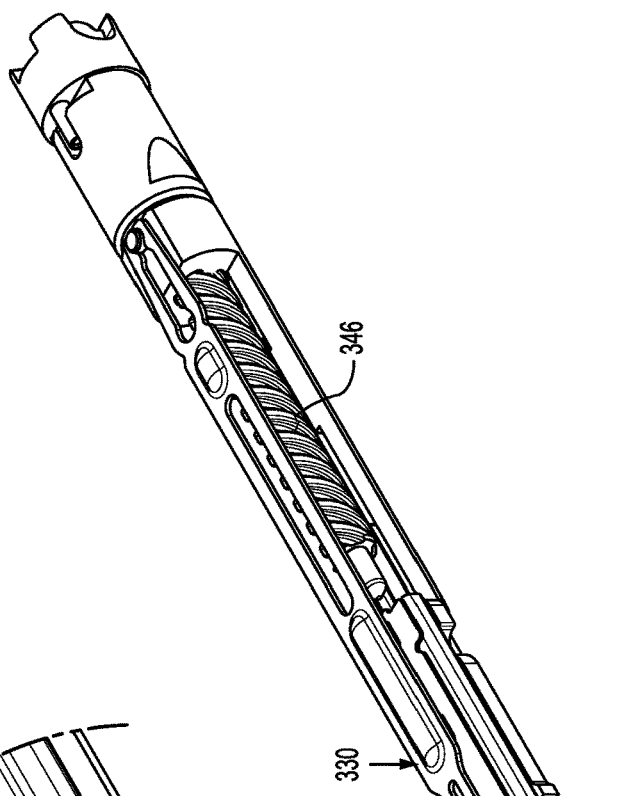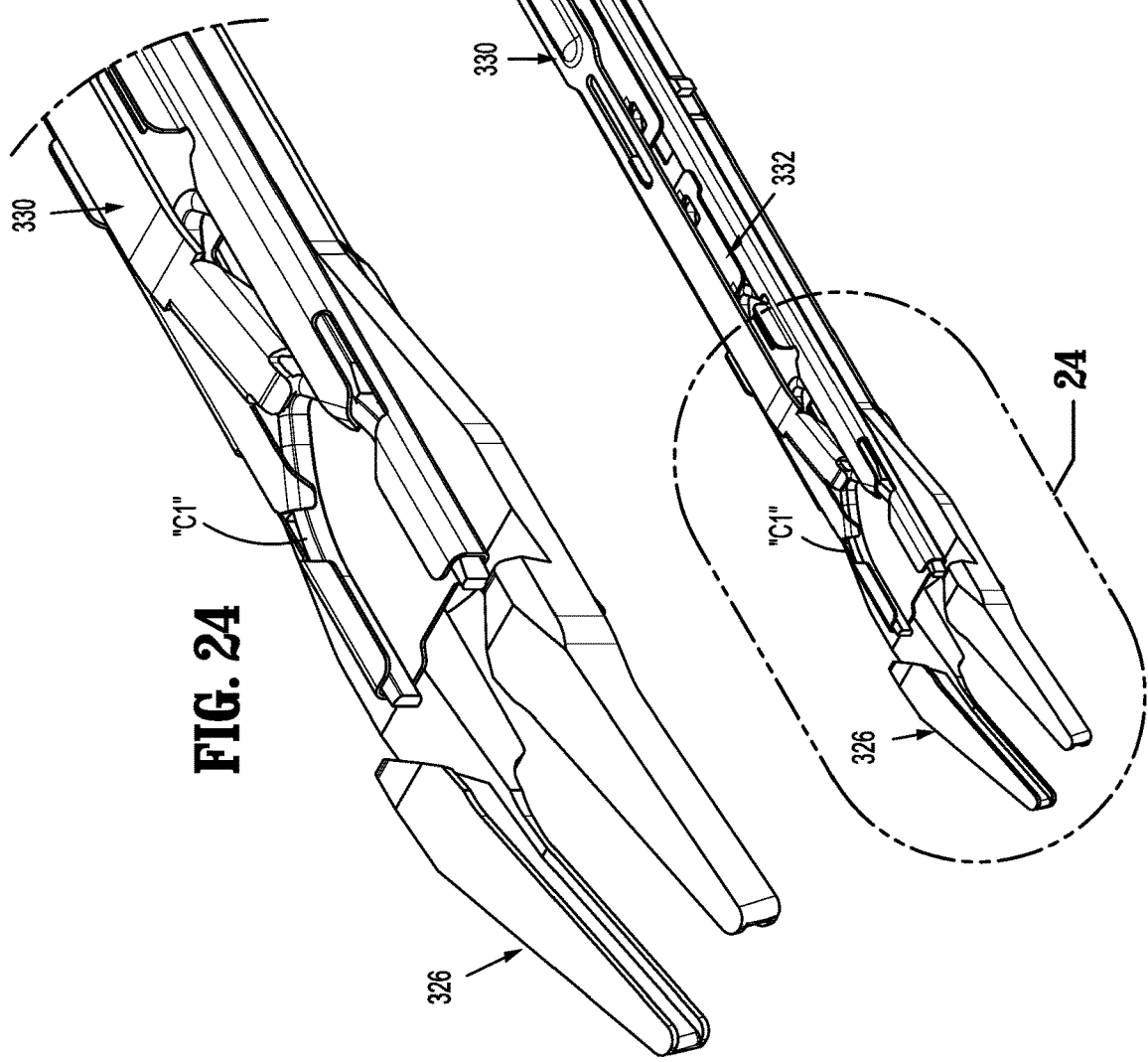

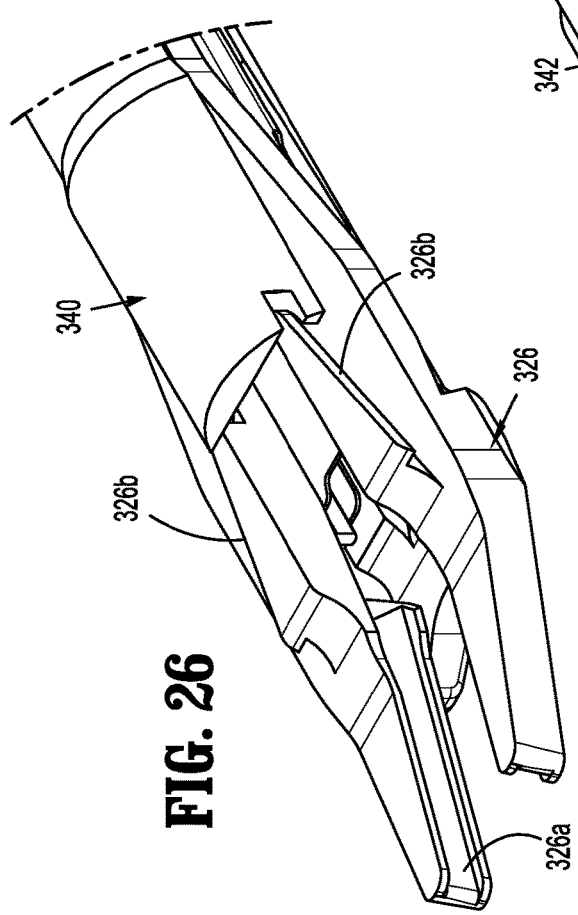
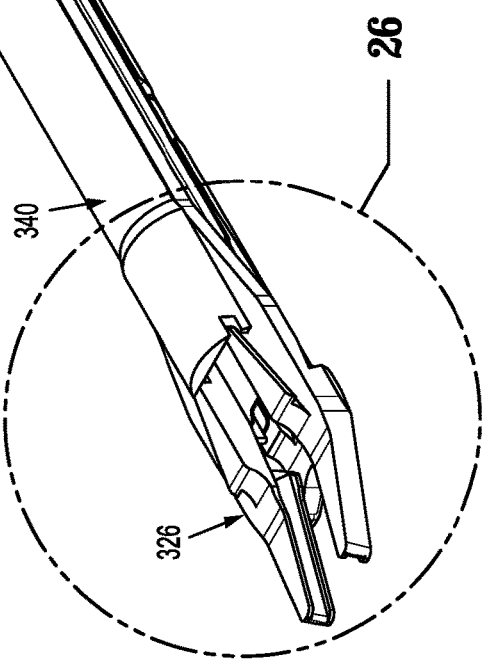

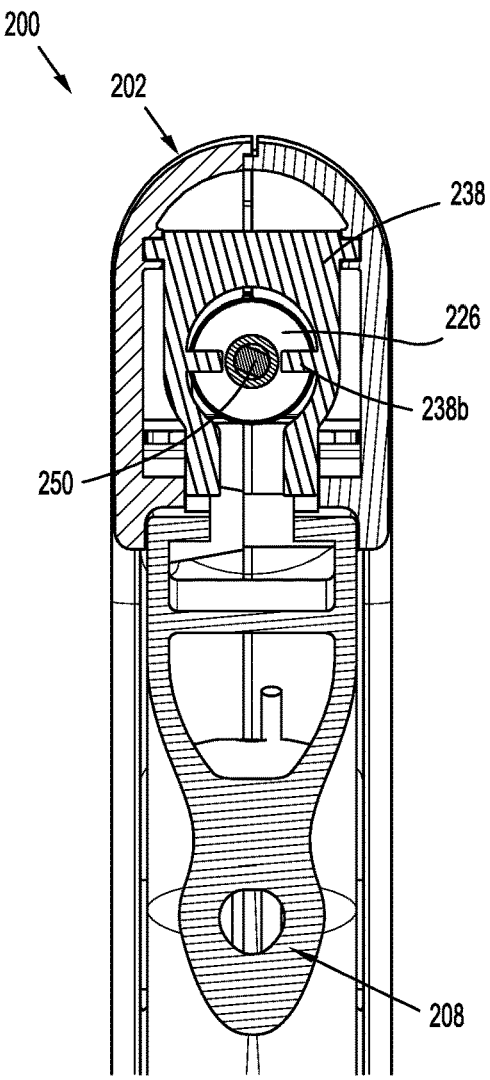
FIG. 30
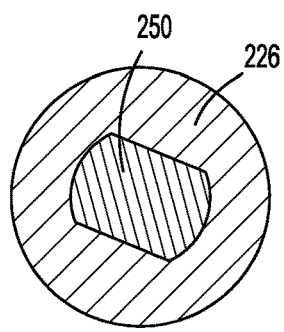
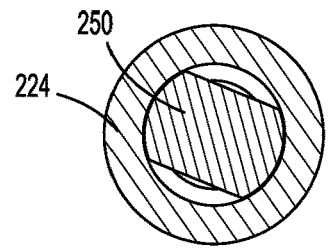
FIG. 31  FIG. 32

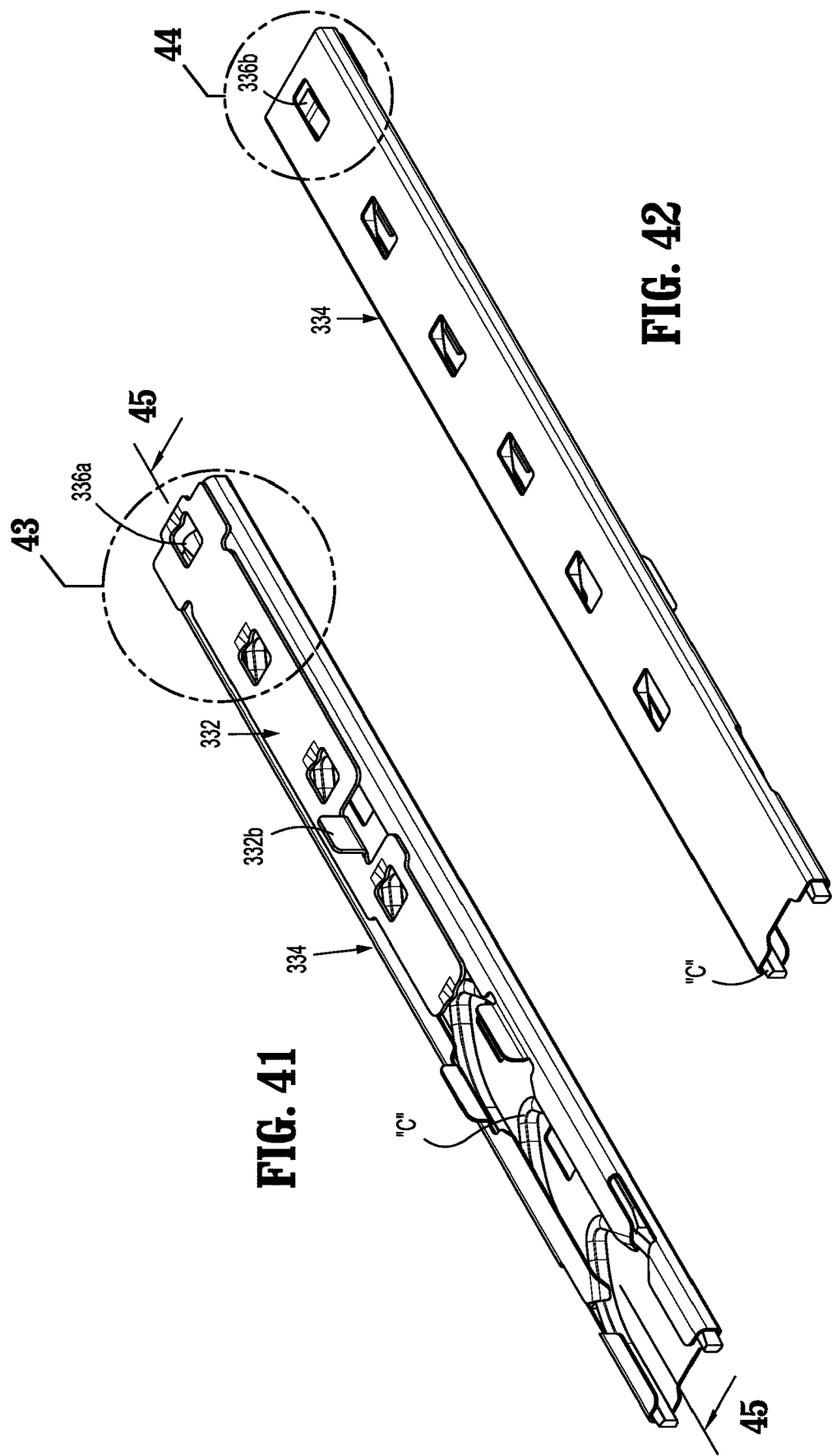

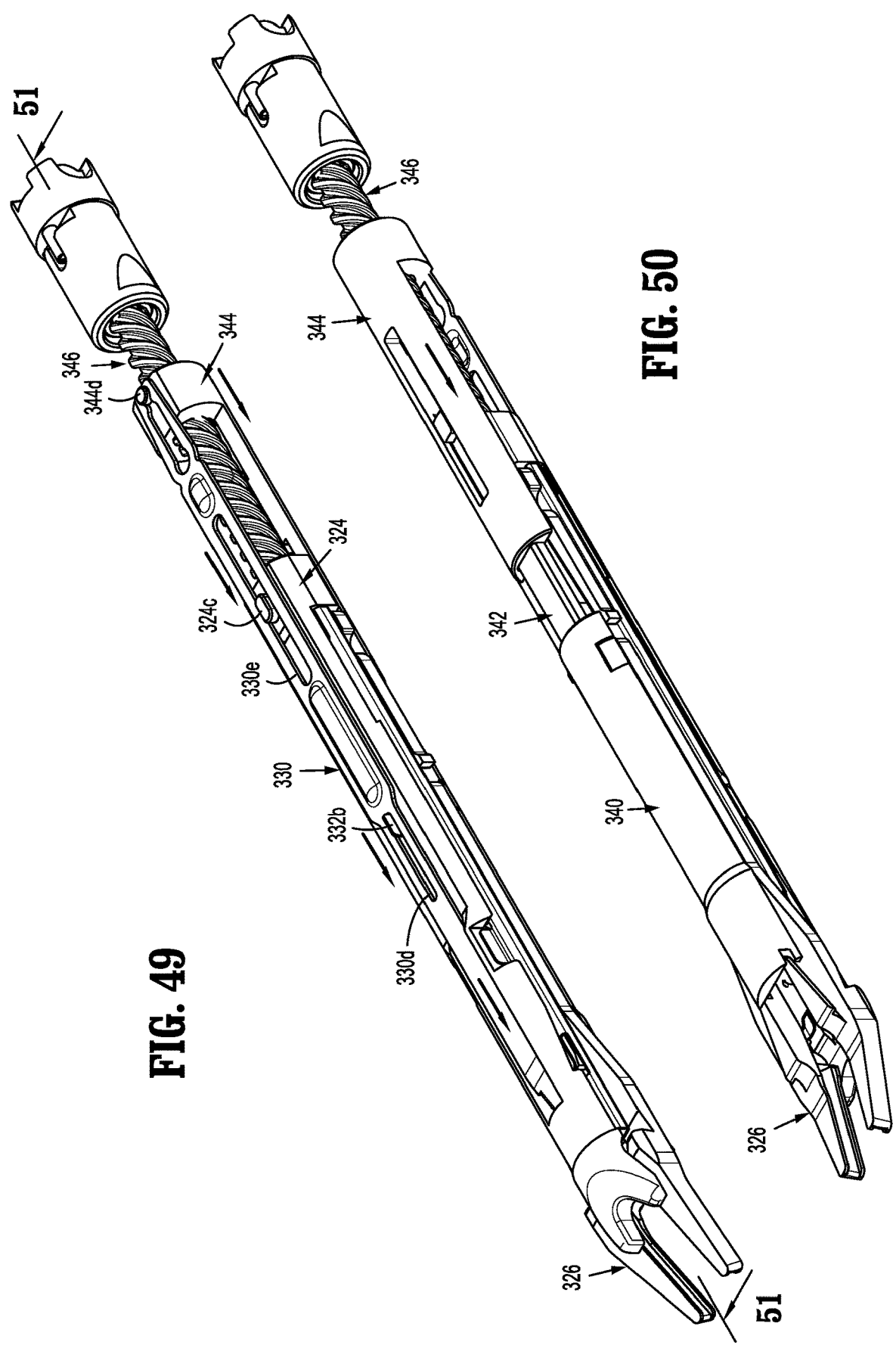

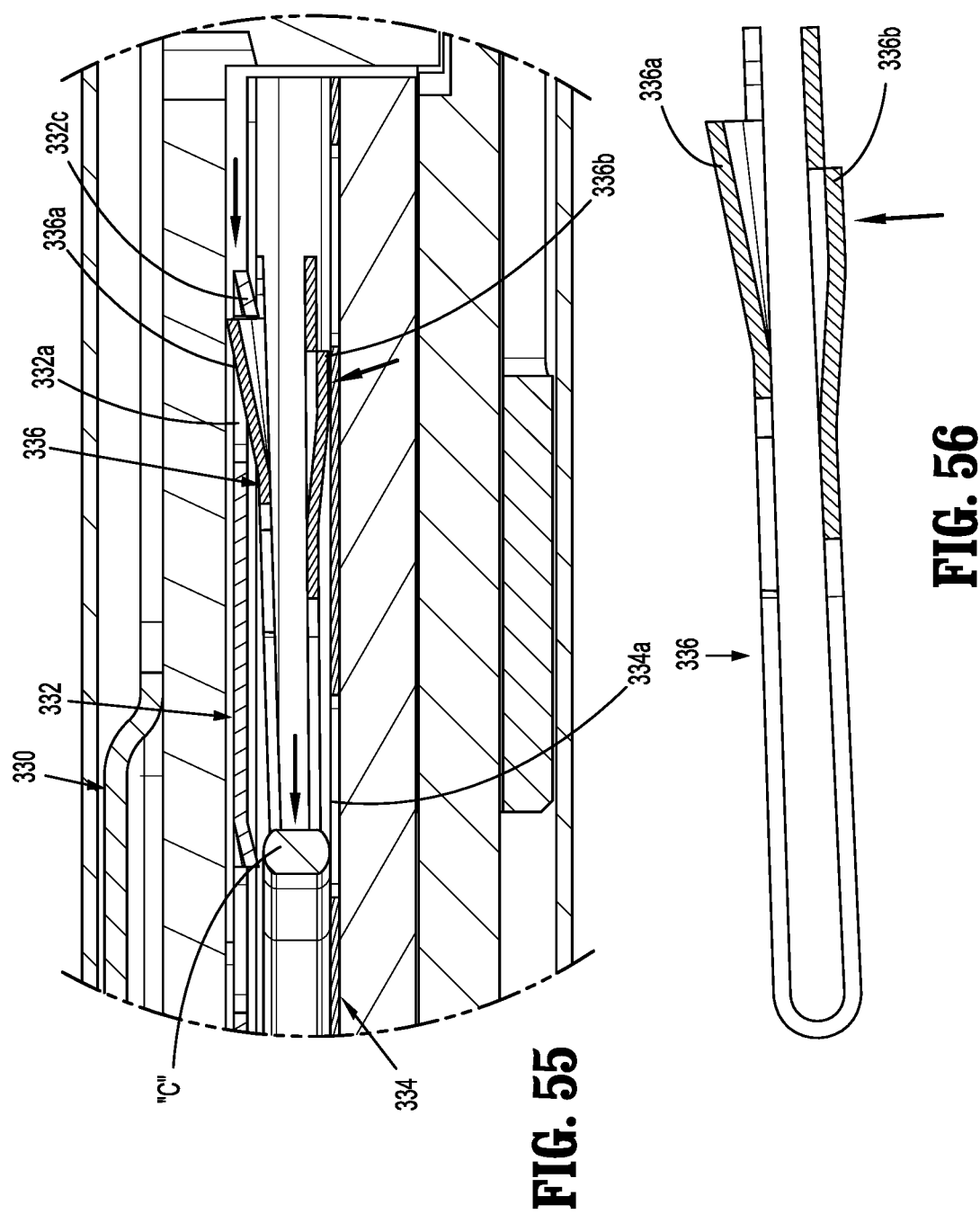

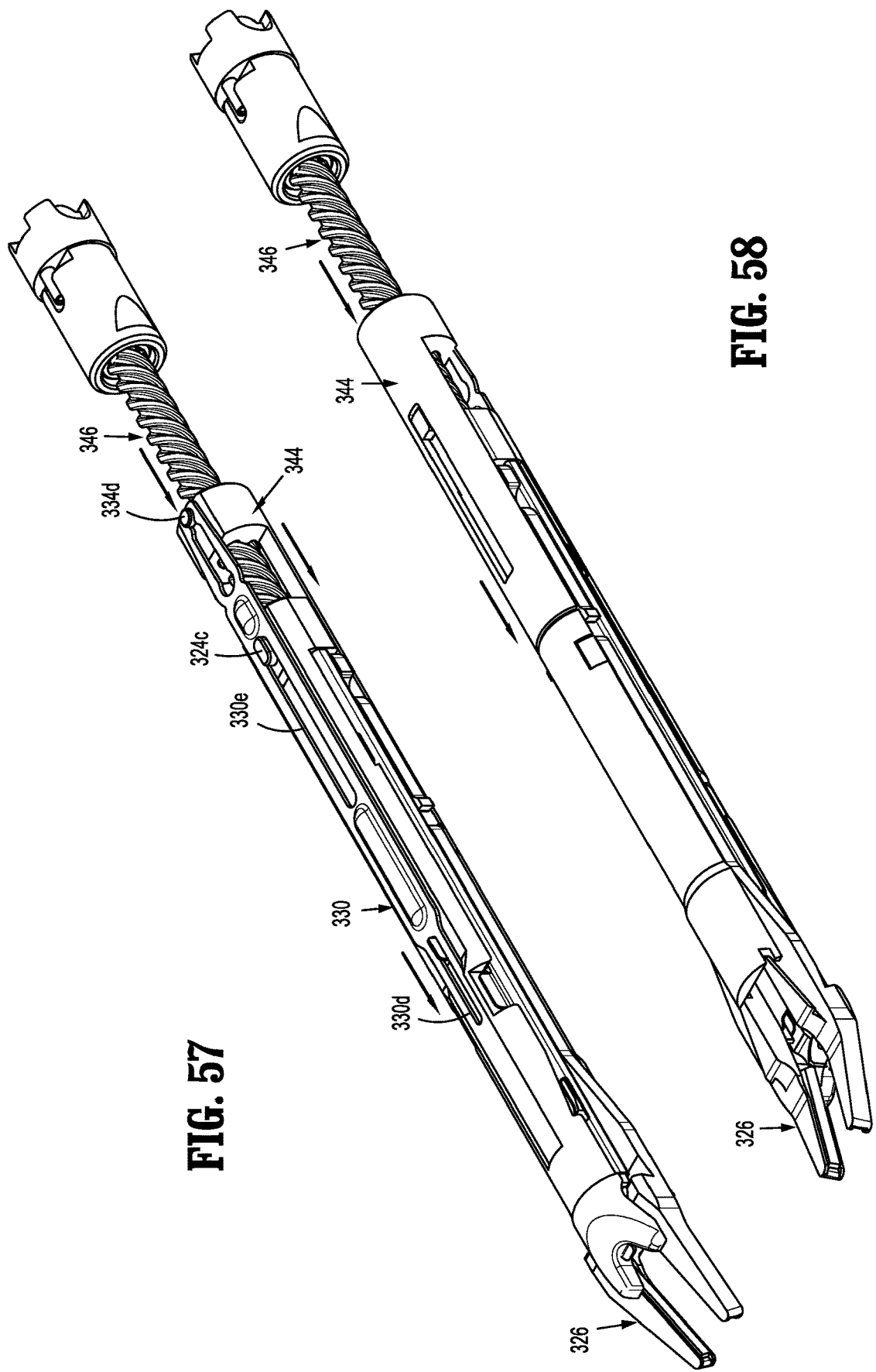

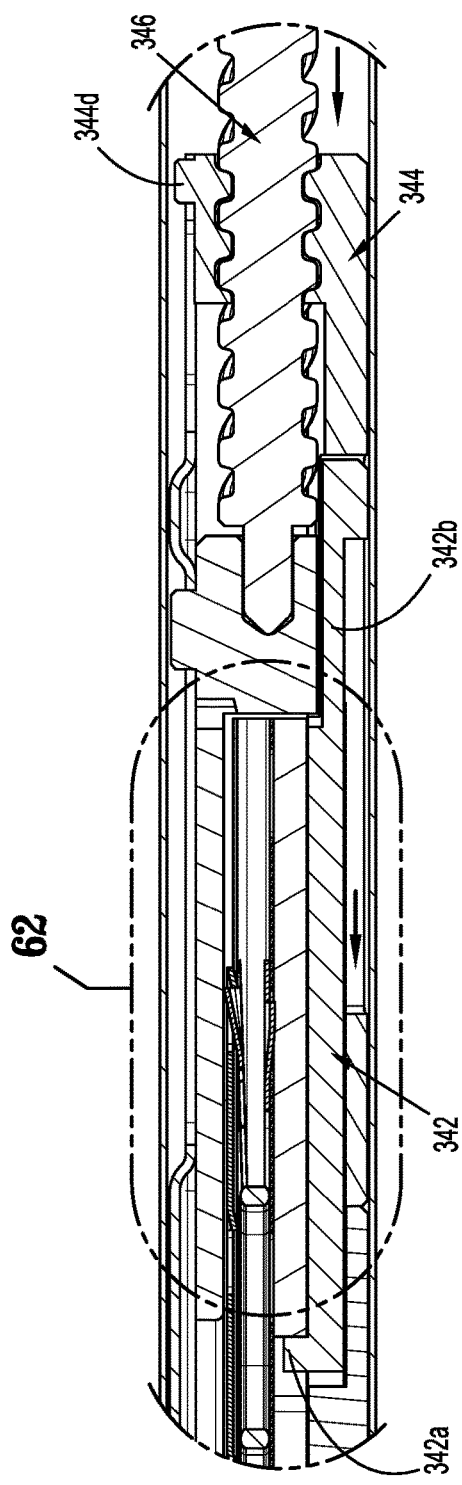
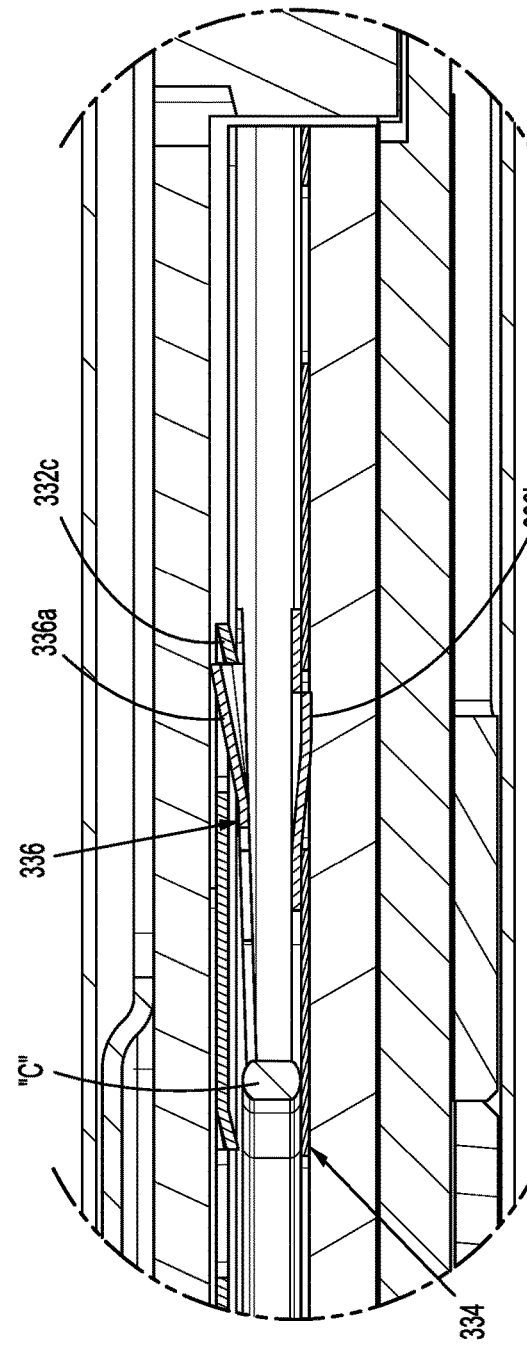
FIG. 61
FIG. 62

ARTICULATING ENDOSCOPIC SURGICAL CLIP APPLIER

CROSS REFERENCE TO RELATED APPLICATIONS

The present application is a Continuation application claiming the benefit of and priority to U.S. patent application Ser. No. 16/299,356, filed on Mar. 12, 2019, which is a Continuation application claiming the benefit of and priority to U.S. patent application Ser. No. 15/151,535, filed May 11, 2016, now U.S. Pat. No. 10,271,854, which is a Continuation application claiming the benefit of and priority to U.S. patent application Ser. No. 14/486,306, filed Sep. 15, 2014, now U.S. Pat. No. 9,393,024, which is a Continuation application claiming the benefit of and priority to U.S. patent application Ser. No. 13/772,998, filed Feb. 21, 2013, now U.S. Pat. No. 8,845,659, which is a Continuation application claiming the benefit of and priority to U.S. patent application Ser. No. 13/004,064, filed on Jan. 11, 2011, now U.S. Pat. No. 8,403,945, which claims the benefit of and priority to U.S. Provisional Application Ser. No. 61/308,093, filed on Feb. 25, 2010, the disclosures of each of the above being hereby incorporated by reference in their entirety.

BACKGROUND

1. Technical Field

The present disclosure relates to surgical clip appliers and, more particularly, to a novel articulating endoscopic surgical clip applier.

2. Background of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such single clip appliers are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 to Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity. One significant design goal is that the surgical clip be loaded between the jaws without any compression of the clip from the loading procedure. Such bending or torque of the clip during loading often has a number of unintended consequences. Such compression during loading may alter slightly the alignment of the clip between the jaws. This will cause the surgeon to remove the clip from between the jaws for discarding the clip. Additionally such preloading compression may slightly compress parts of the clip and change a geometry of the clip. This will cause the surgeon to remove the compressed clip from between the jaws for discarding the clip.

Endoscopic or laparoscopic procedures are often performed remotely from the incision. Consequently, application of clips may be complicated by a reduced field of view or reduced tactile feedback for the user at the proximal end of the device. It is therefore desirable to improve the operation of the instrument by providing an instrument that is capable of articulating.

SUMMARY

The present disclosure relates to novel articulating endoscopic surgical clip appliers.

BRIEF DESCRIPTION OF THE DRAWINGS

The present clip applier will be more fully appreciated as the same becomes better understood from the following detailed description when considered in connection with the following drawings, in which:

FIG. 14 is a front, perspective view of the surgical clip applier of FIGS. 1-4, illustrating a rotation of the shaft assembly thereof;

FIG. 15 is a cross-sectional view as taken through 15-15 of FIG. 14;

FIG. 17 is a perspective view of the clip applier end effector assembly of FIG. 16, with an outer tube removed therefrom;

FIG. 18 is a perspective view of the clip applier end effector assembly of FIG. 16, with the outer tube and a pusher bar removed therefrom;

FIG. 19 is a perspective view of the clip applier end effector assembly of FIG. 16, with the outer tube, the pusher bar and an upper housing removed therefrom;

FIG. 20 is a perspective view of the clip applier end effector assembly of FIG. 16, with the outer tube, the pusher bar, the upper housing and an advancer plate removed therefrom;

FIG. 21 is a perspective view of the clip applier end effector assembly of FIG. 16, with the outer tube, the pusher bar, the upper housing, the advancer plate and a clip carrying channel removed therefrom;

FIG. 22 is a perspective view of the clip applier end effector assembly of FIG. 16, with the outer tube, the pusher bar, the upper housing, the advancer plate, the clip carrying channel and the jaws removed therefrom;

FIG. 23 is a distal, top, perspective view of the clip applier end effector assembly of FIG. 17;

FIG. 24 is an enlarged view of the indicated area of detail of FIG. 23;

FIG. 25 is a distal, bottom, perspective view of the clip applier end effector assembly of FIG. 17;

FIG. 26 is an enlarged view of the indicated area of detail of FIG. 25;

FIG. 30 is a cross-sectional view as taken through 30-30 of FIG. 29;

FIG. 31 is a cross-sectional view as taken through 31-31 of FIG. 29;

FIG. 32 is a cross-sectional view as taken through 32-32 of FIG. 29;

FIG. 41 is a top, perspective view of the clip channel, advancer plate, clip follower and stack of clips, shown in an assembled condition;

FIG. 42 is a bottom, perspective view of the clip channel, advancer plate, clip follower and stack of clips, shown in an assembled condition;

FIG. 49 is a top, perspective view of the end effector assembly of the surgical clip applier, with the outer tube removed, during the initial actuation of the trigger of the surgical clip applier;

FIG. 50 is a bottom, perspective view of the end effector assembly of the surgical clip applier, with the outer tube removed, during the initial actuation of the trigger of the surgical clip applier;

FIG. 55 is an enlarged view of the indicated area of detail of FIG. 54;

FIG. 56 is a longitudinal, cross-sectional view of the clip follower as illustrated in FIG. 55;

FIG. 57 is a top, perspective view of the end effector assembly of the surgical clip applier, with the outer tube removed, during the further actuation of the trigger of the surgical clip applier;

FIG. 58 is a bottom, perspective view of the end effector assembly of the surgical clip applier, with the outer tube removed, during the further actuation of the trigger of the surgical clip applier;

FIG. 61 is an enlarged view of the indicated area of detail of FIG. 59;

FIG. 62 is an enlarged view of the indicated area of detail of FIG. 61;

DETAILED DESCRIPTION OF EMBODIMENTS

Figure 1:
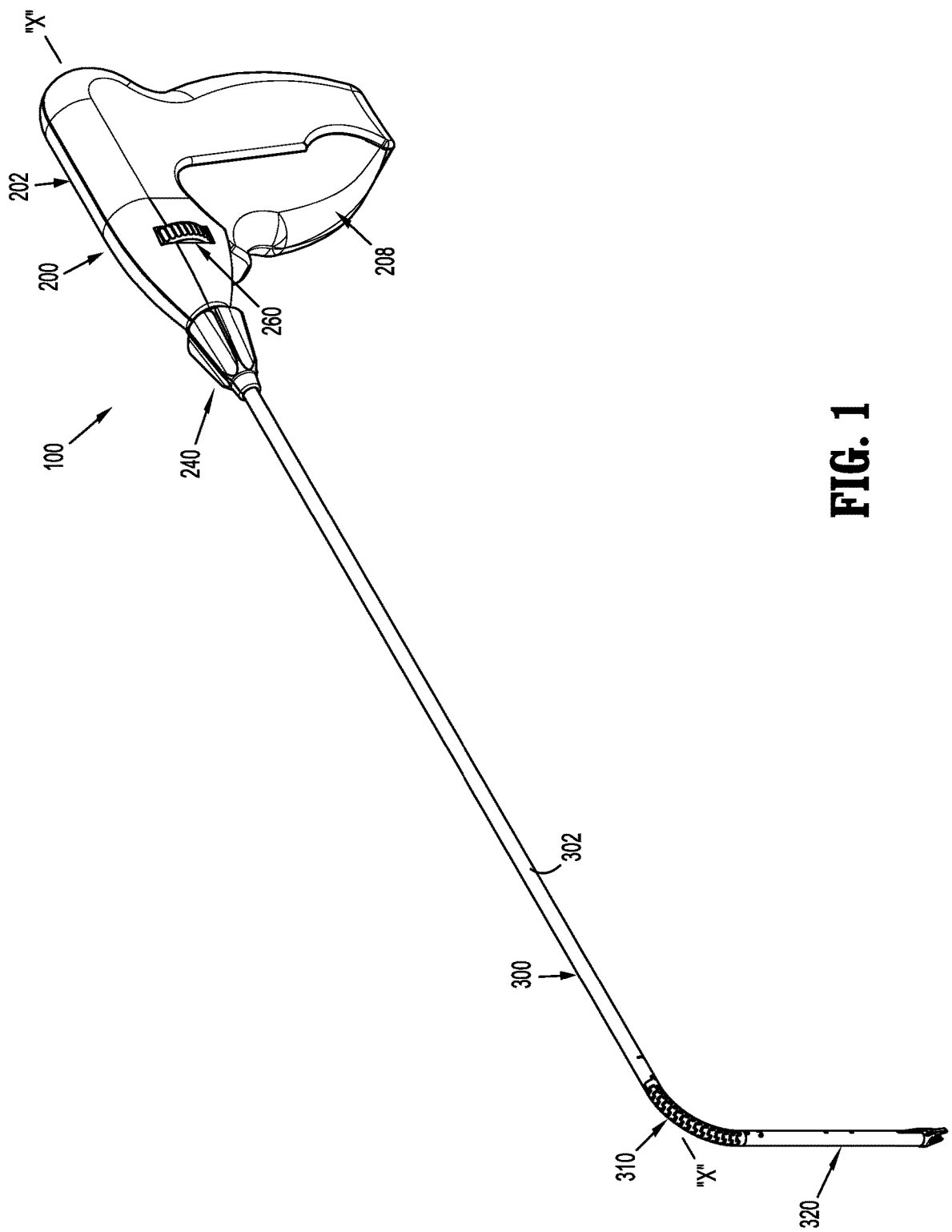
FIG. 1 is a front, perspective view of a surgical clip applier according to an embodiment of the present disclosure, shown in an articulated condition.
Figure 2:
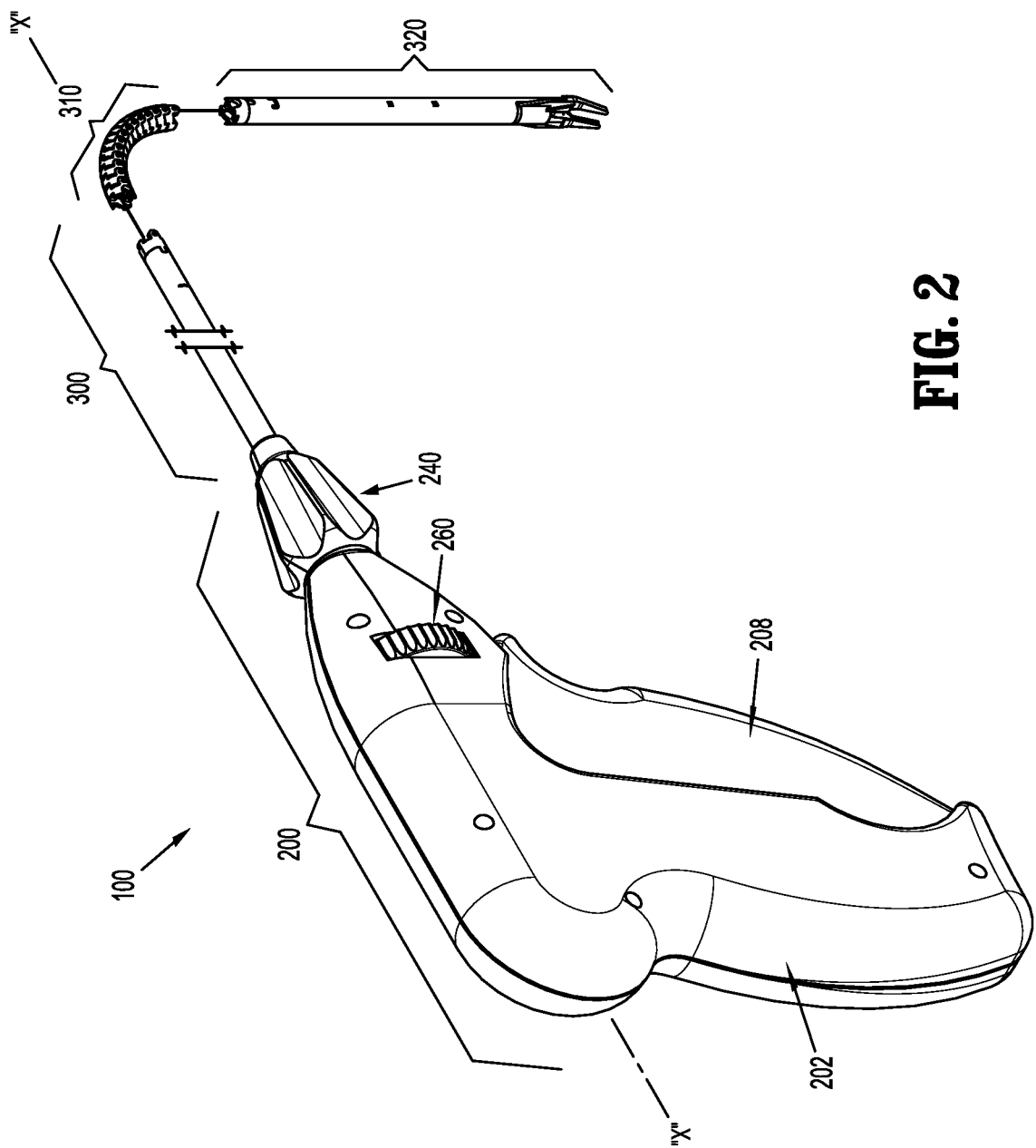
FIG. 2 is a rear, perspective view of the clip applier of FIG. 1, shown in an articulated condition.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-25, a surgical clip applier in accordance with an embodiment of the present disclosure is generally designated as 100. Clip applier 100 includes a handle assembly 200 and an articulating endoscopic portion including a shaft assembly 300 extending distally from handle assembly 200.

Referring now to FIGS. 1-8, handle assembly 200 of surgical clip applier 100 is shown. Handle assembly 200 includes a housing 202 having a first or right side half-section 202a and a second or left side half-section 202b. Handle assembly 200 includes a trigger 208 pivotably supported between right side half-section 202a and left side half-section 202b. Trigger 208 is biased to an un-actuated position by a biasing member 210, in the form of a spring or the like. Housing 202 of handle assembly 200 may be formed of a suitable plastic material.

Figure 3:
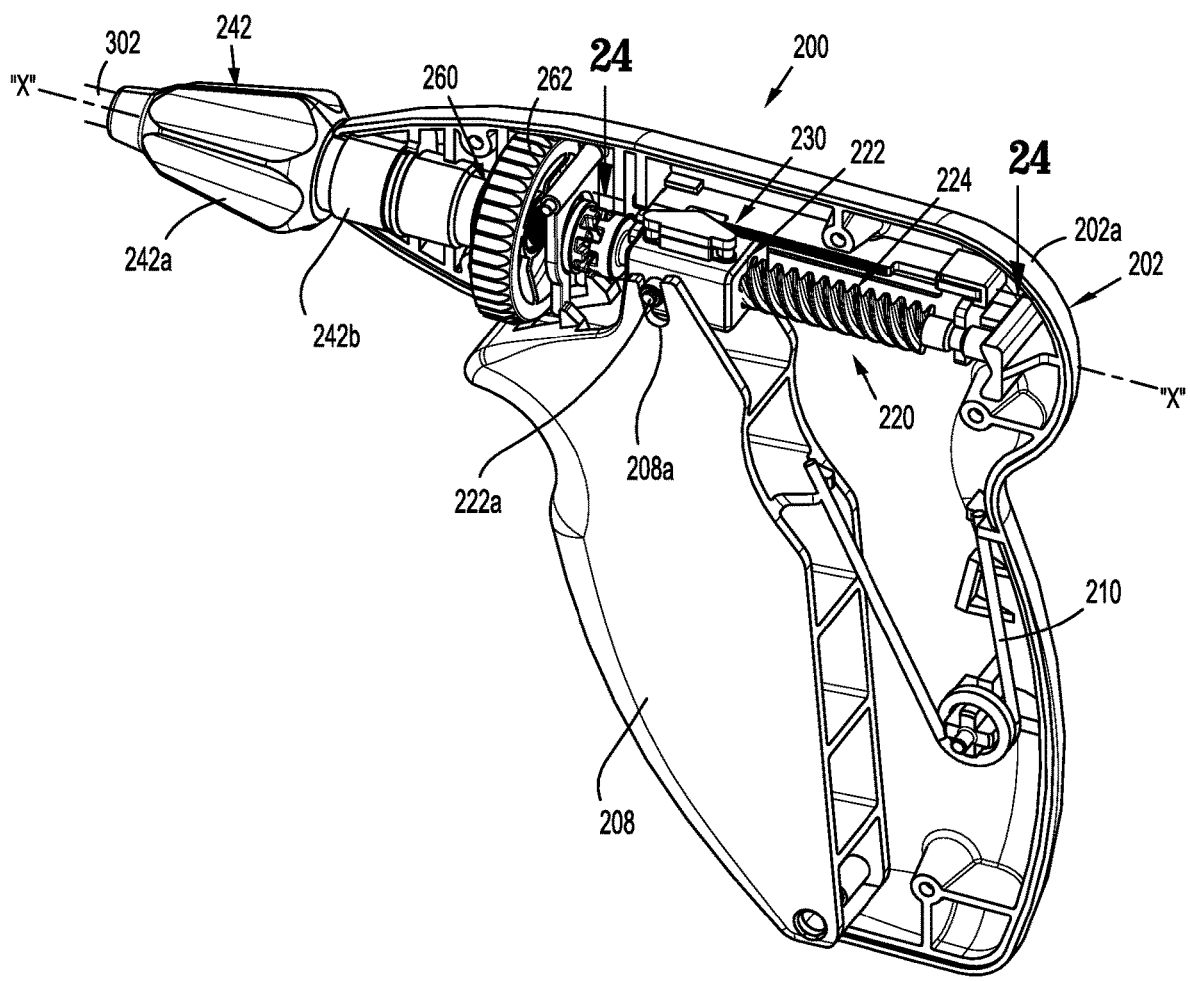
FIG. 3 is a rear, left-side, perspective view of a handle assembly of the surgical clip applier of FIGS. 1 and 2, with a housing half-section removed therefrom.
Figure 4:
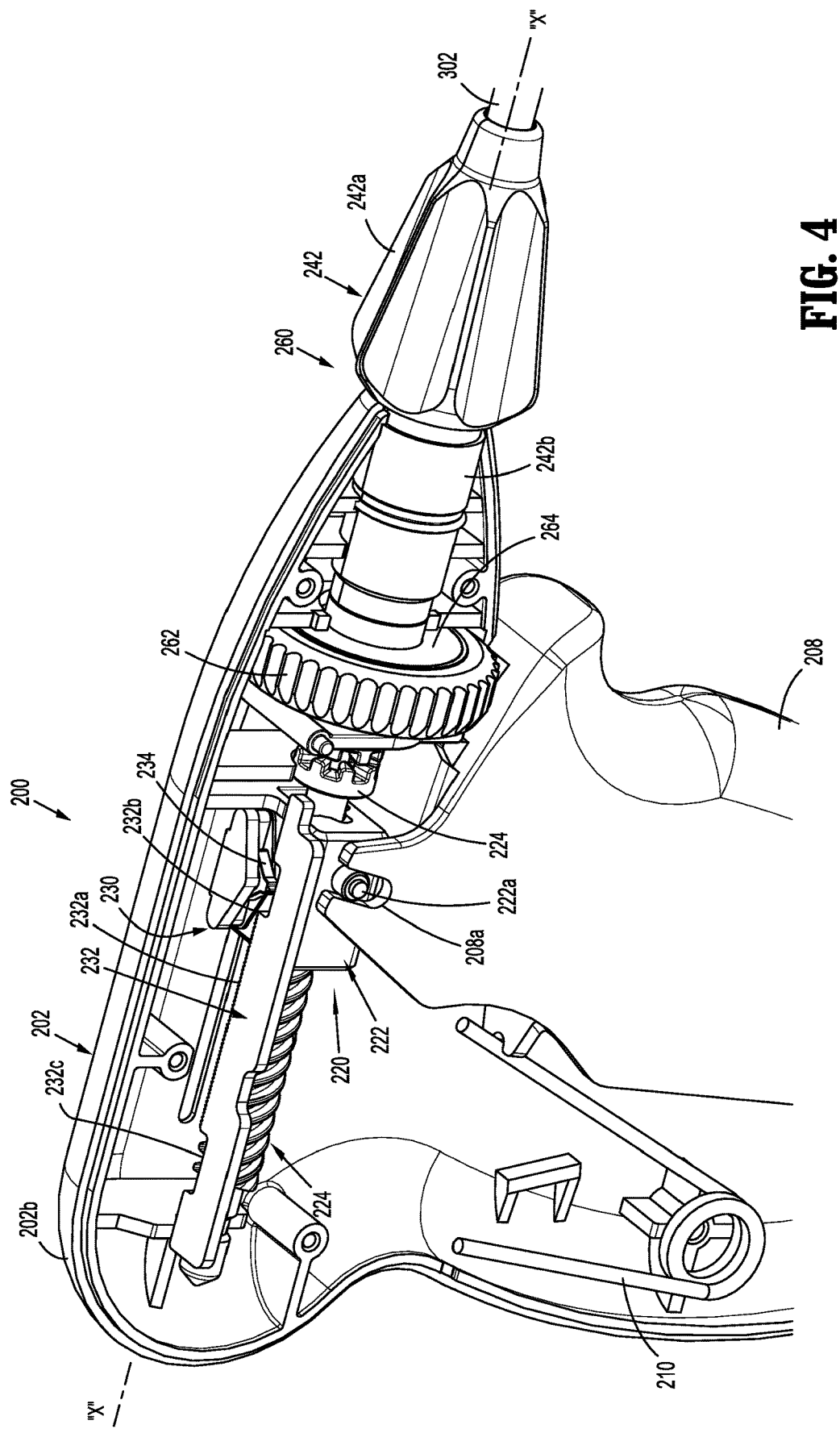
FIG. 4 is a front, right-side, perspective view of the handle assembly of the surgical clip applier of FIGS. 1 and 2, with a housing half-section removed therefrom.

As seen in FIGS. 3-4, housing 202 supports a drive assembly 220 between right side half-section 202a and left side half-section 202b. Drive assembly 220 includes a drive block 222 translatably, slidably supported between right side half-section 202a and left side half-section 202b of housing 202, for movement thereof along a longitudinal axis "X" of clip applier 100. Drive block 222 includes nubs 222a projecting from opposed lateral sides thereof for pivotably and slidably connection in elongated channels 208a formed in trigger 208. Drive block 222 defines a threaded or helical lumen 222b therethrough.

As seen in FIGS. 3-6, handle assembly 200 further includes a ratchet mechanism 230 disposed in housing 202. Ratchet mechanism 230 includes a toothed-rack 232 defined or supported in housing 202, and a pawl 234 pivotally supported on drive block 222 at a location wherein pawl 234 is in substantial operative engagement with toothed-rack 232.

Pawl 234 includes a pawl tooth 234a which is selectively engageable with the teeth of rack 232. Pawl tooth 234a is engageable with the teeth of rack 232 to restrict longitudinal movement of drive block 222 and, in turn, trigger 208. A pawl spring 236 is provided to bias pawl 234 into operative engagement with the teeth of rack 232.

Toothed-rack 232 includes a plurality of teeth 232a interposed between a distal reversing recess 232b and a proximal reversing recess 232c. In use, with pawl in either distal reversing recess 232b or proximal reversing recess 232c, as drive block 222, and thus pawl 234, is translated in a first direction relative to tooth-rack 232, tooth 234a is pulled across the teeth 232a of toothed-rack 232. The translation of drive block 222 can not be reversed until tooth 234a of pawl 234 reaches the other of either distal reversing recess 232b or proximal reversing recess 232c of toothed-rack 232, such that an orientation of pawl 234 may be re-set or reversed. Once the orientation of pawl 234 is either re-set or reversed, drive block 222 may be translated in an opposite direction. As so constructed, it is apparent that the direction of translation of drive block 222 can not be reversed until a complete stoke or travel length of drive block 222 is accomplished.

Figure 28:
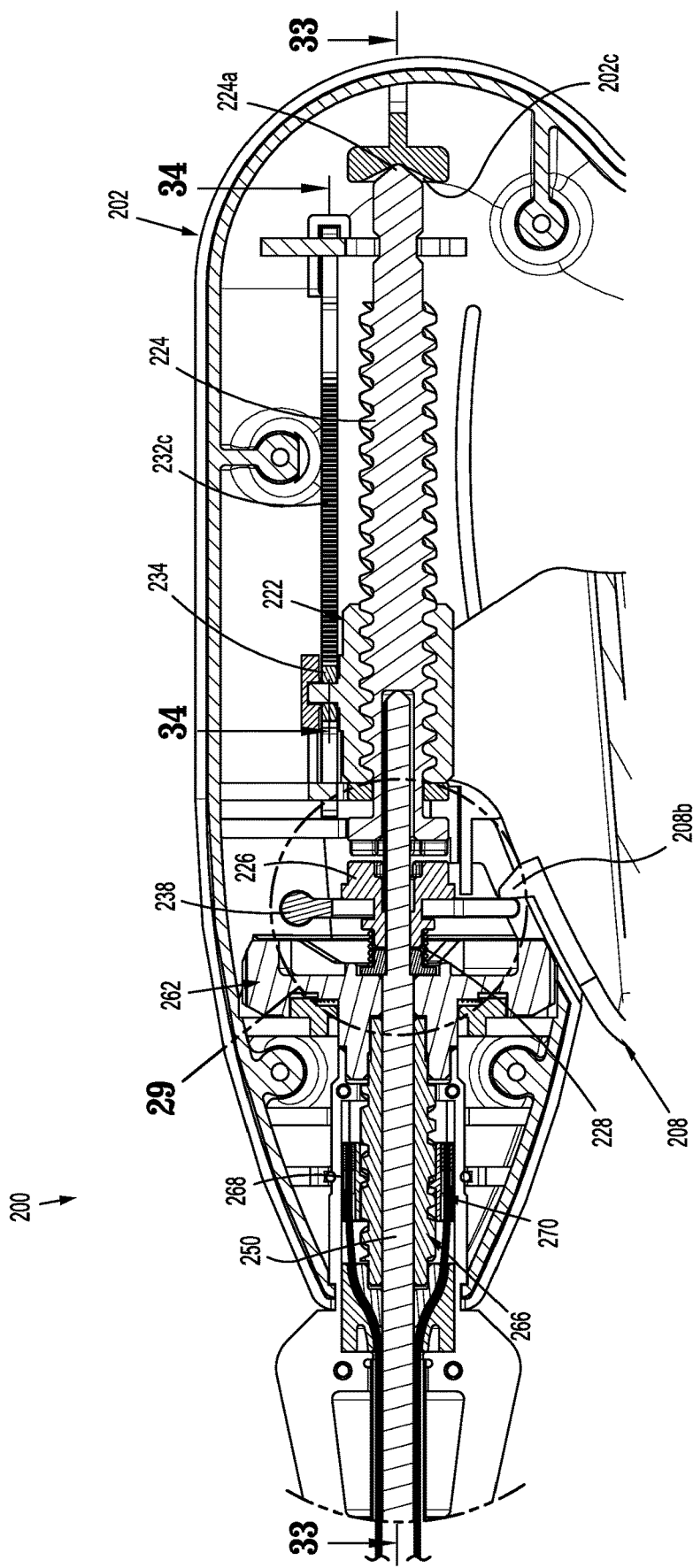
FIG. 28 is an enlarged view of the indicated area of detail of FIG. 27.

With continued reference to FIGS. 3-6, drive assembly 220 further includes a drive screw 224 rotatably supported within housing 202. Drive screw 224 includes a proximal tip 224a for establishing a point contact within a cup 202c (see FIG. 28) provided in housing 202. Drive screw 224 further includes an outer helical thread 224b extending along a length thereof and configured to mate within helical lumen 222b of drive block 222. Drive screw 224 further includes a crown of teeth 224c supported at a distal end thereof. In use, as trigger 208 is actuated trigger 208 translates drive block 222 through housing 202. As drive block 222 is translated through housing 202, helical lumen 222b of drive block 222 cooperates with helical thread 224b of drive screw 224 to result in rotation of drive screw 224.

Figure 16:
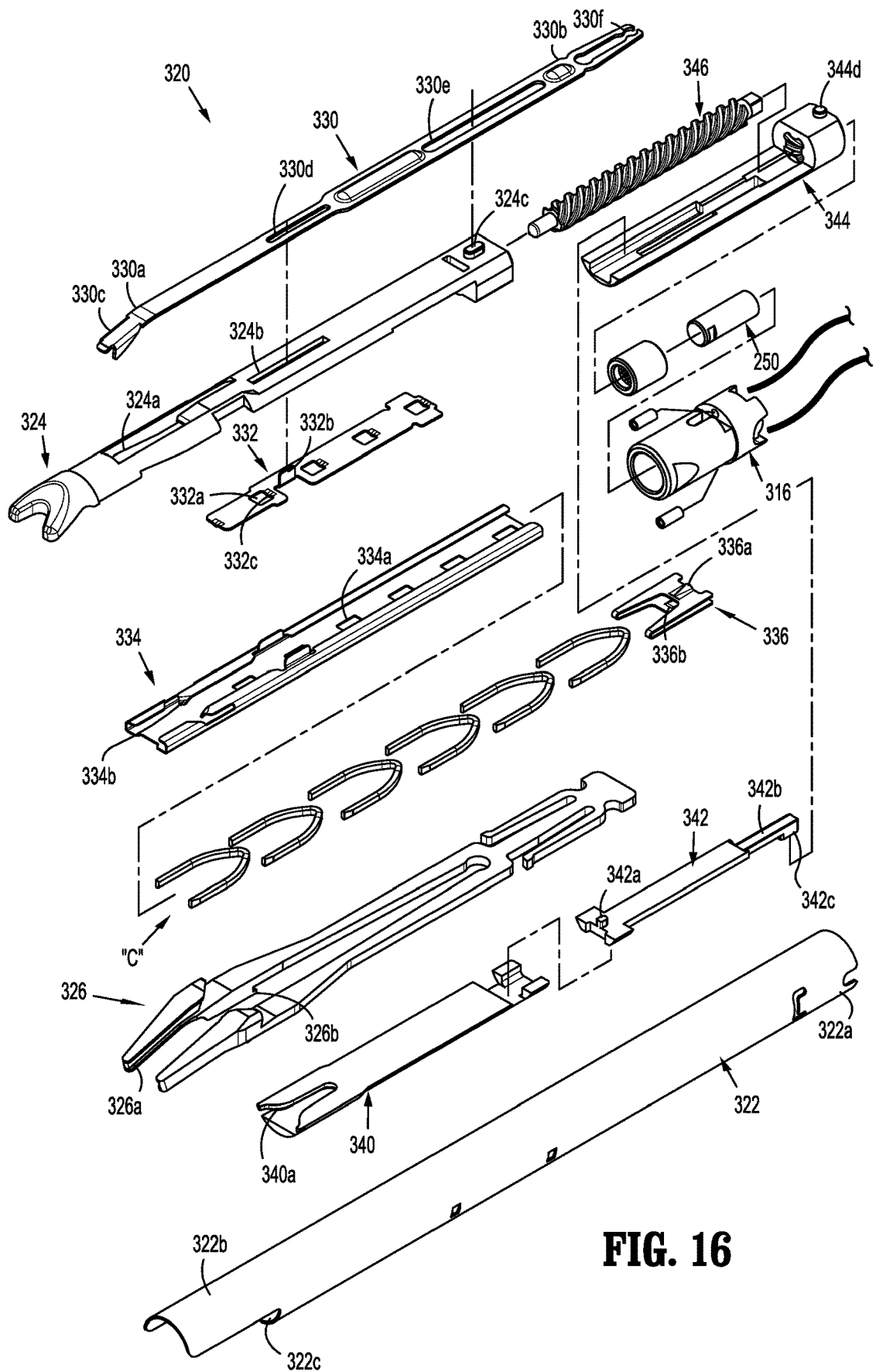
FIG. 16 is a perspective view, with parts separated, of a clip applying end effector assembly of the clip applier of FIGS. 1-4.
Figure 27:
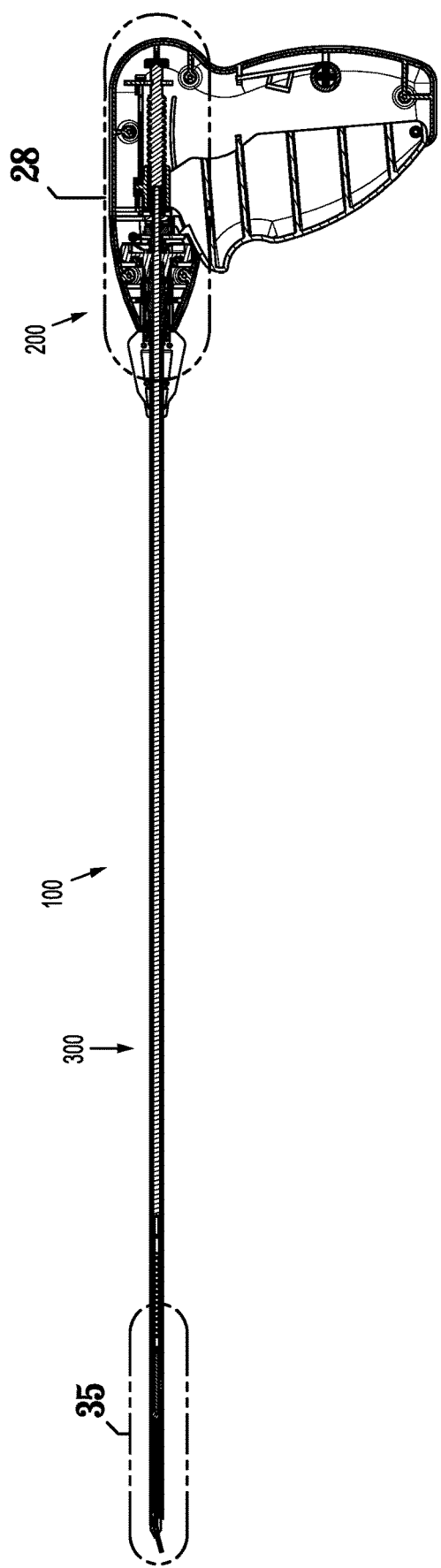
FIG. 27 is a longitudinal, side-elevational, cross-sectional view of the clip applier of FIGS. 1-4.

Drive assembly 220 further includes a clutch gear 226 rotatably supported in housing 202 and keyed to drive shaft 250 (see FIGS. 16 and 31). Clutch gear 226 defines a crown of gear teeth 226a configured and dimensioned to cooperate and selectively engage the crown of teeth 224c of drive screw 224. Clutch gear 226 may be biased, by a biasing member 228, such that crown of teeth 226a thereof is in engagement with the crown of teeth 224c of drive screw 224. Clutch gear 226 defines an outer annular race 226d therein.

Drive assembly 220 further includes a clutch bracket 238 pivotally supported in housing 202. Clutch bracket 238 includes a pair of legs 238a extending around clutch gear 226, and a boss 238b, extending from each leg 238a and into annular race 226d of clutch gear 226. A free end 238c of each leg 238a extends an amount sufficient to engage a rib 208b formed on trigger 208. In use, as clutch bracket 238 is pivoted distally (due to biasing member 228) and proximally, due to the squeezing and releasing of trigger 208, clutch bracket 238 approximates and separates clutch gear 226 with the crown of teeth 224c of drive screw 224.

With reference to FIGS. 1-7, handle assembly 200 of clip applier 100 further includes a rotation assembly 240 having a rotation knob 242 rotatably supported on and in housing 202 at a distal end thereof. Knob 242 includes grip portion 242a disposed externally of housing 202 and a stem portion 242b disposed within housing 202. Knob 242 defines a lumen 242c therethrough. Stem portion 242b defines a pair of opposed, longitudinally extending channels or grooves $242b_1$, $242b_2$ formed in the wall of lumen 242c.

As seen in FIGS. 1-15, handle assembly 200 also includes an articulation assembly 260 supported on or in housing 202.

Figure 7:
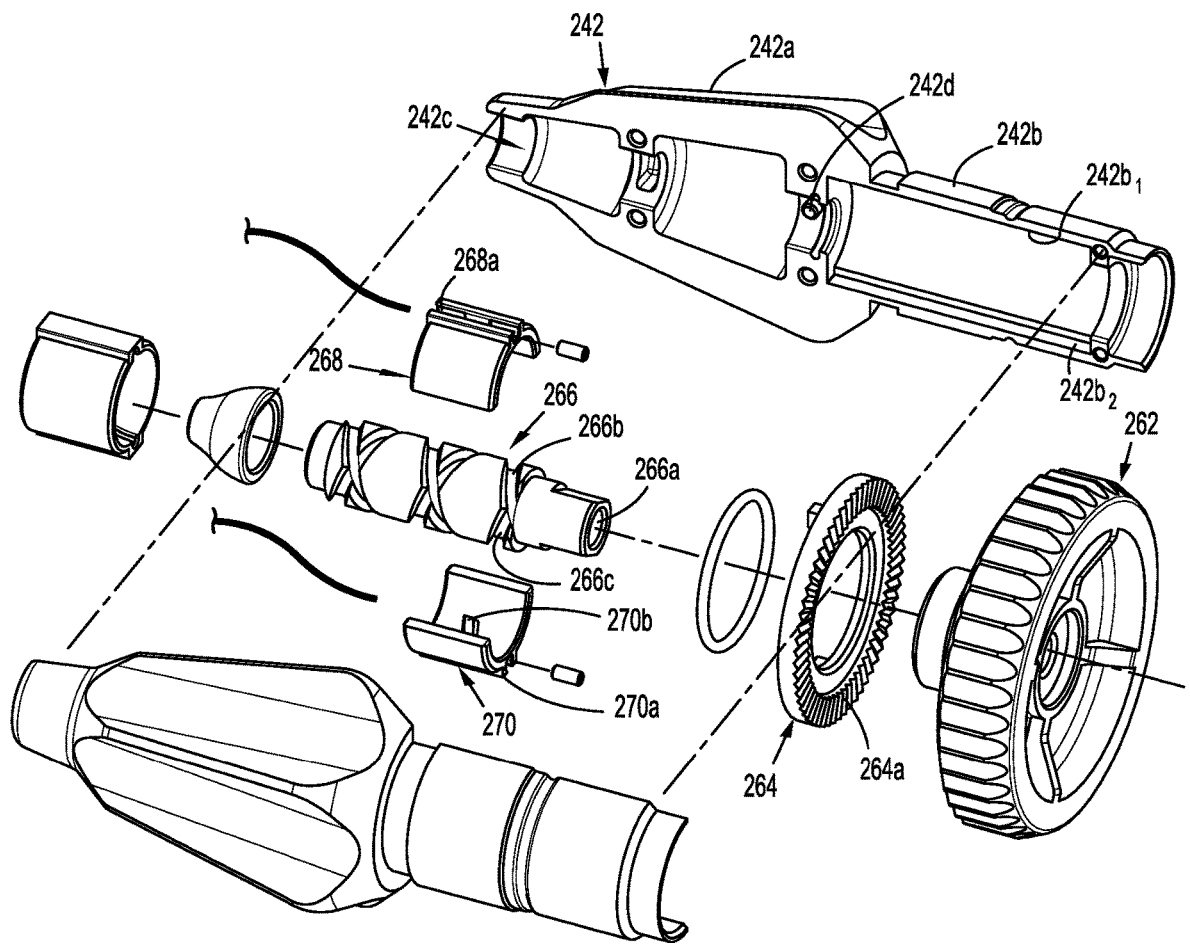
FIG. 7 is an enlarged perspective view of the indicated area of detail of FIG. 5.
Figure 8:
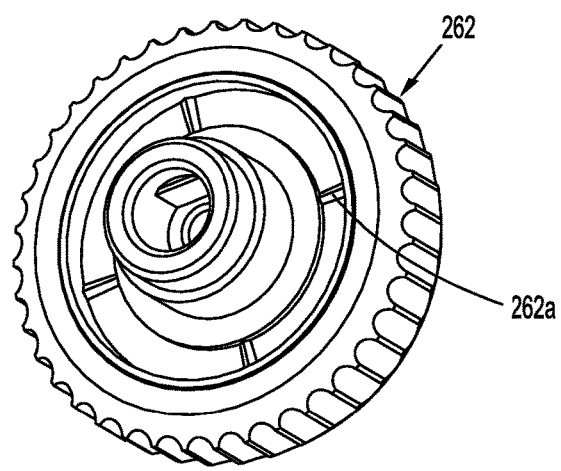
FIG. 8 is a front, perspective view of an articulation dial of the surgical clip applier of FIGS. 1-4.
Figure 9:
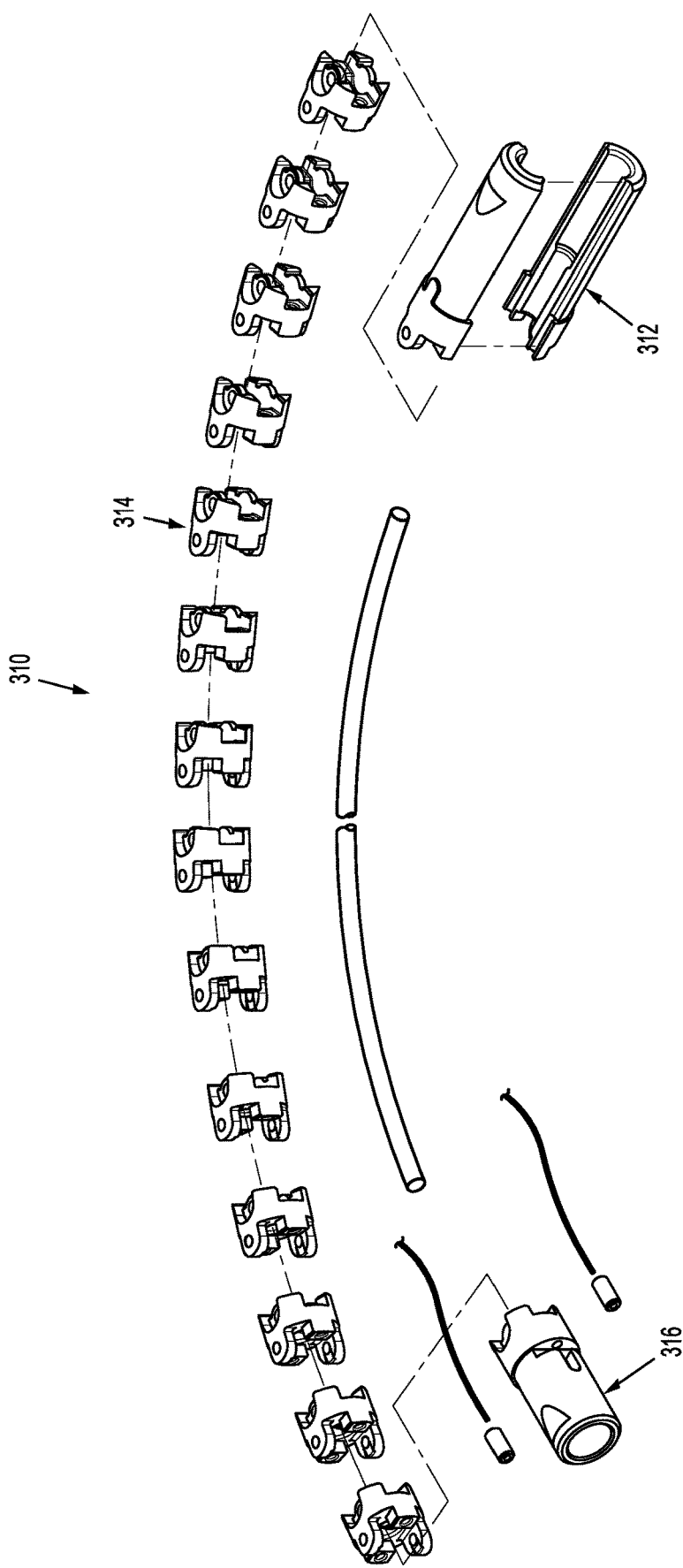
FIG. 9 is a perspective view, with parts separated, of an articulating neck assembly of the surgical clip applier of FIGS. 1-4.
Figure 10:
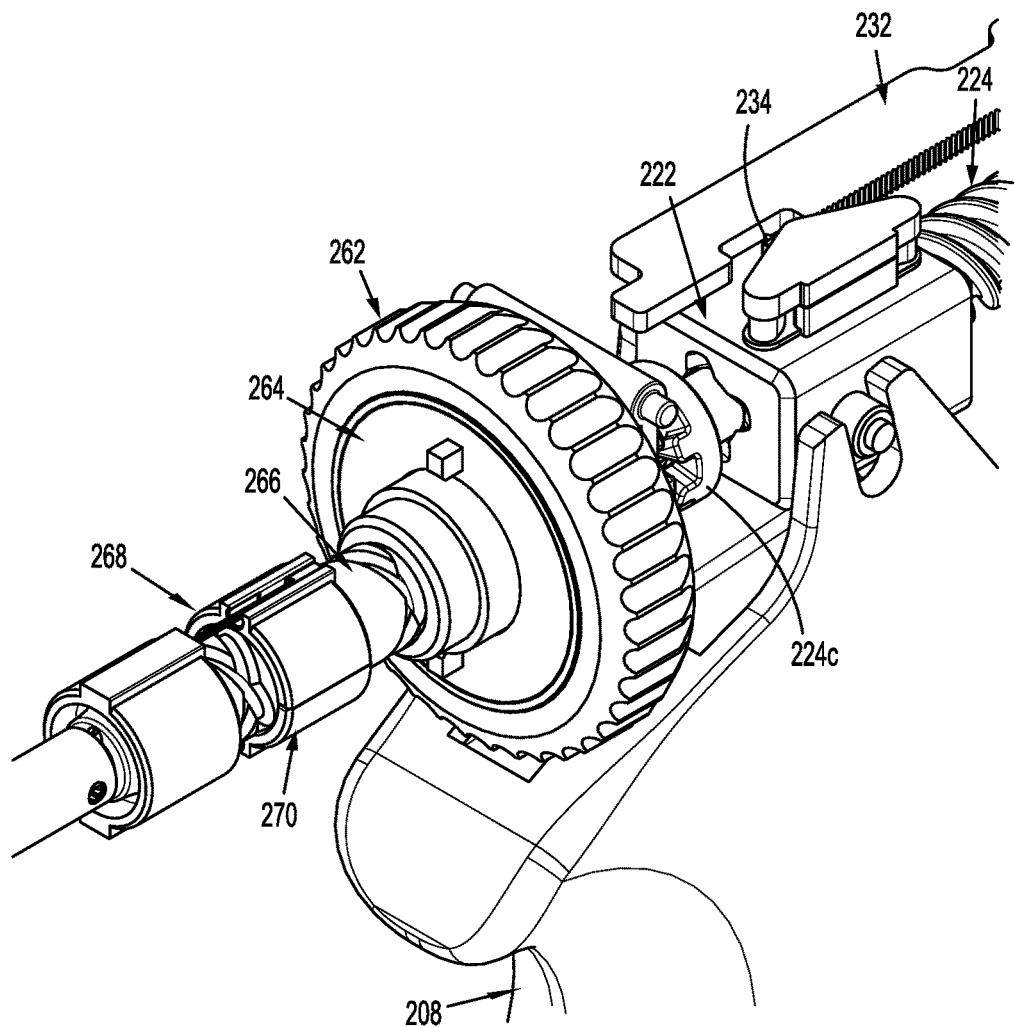
FIG. 10 is a front, perspective view of the handle assembly of the surgical clip applier of FIGS. 1-4, with the housing removed therefrom, illustrating an articulation assembly in an un-actuated condition.
Figure 11:
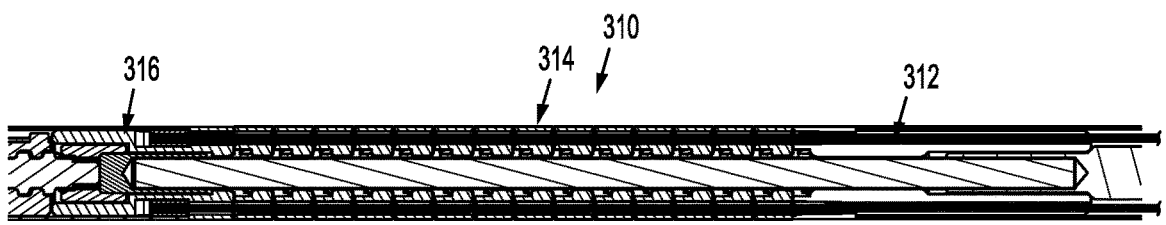
FIG. 11 is a longitudinal, cross-sectional view of the neck assembly of FIG. 9, shown in an un-articulated condition.
Figure 12:
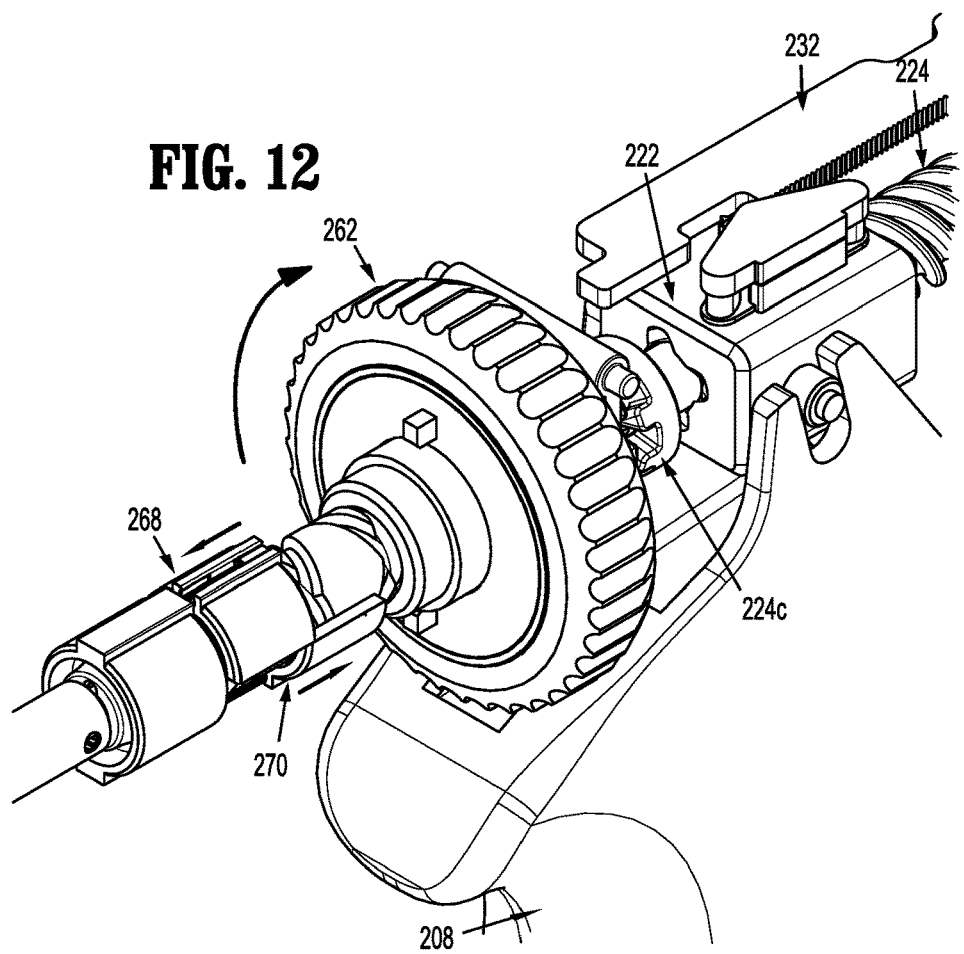
FIG. 12 is a front, perspective view of the handle assembly of the surgical clip applier of FIGS. 1-4, with the housing removed therefrom, illustrating the articulation assembly in an actuated condition.
Figure 13:
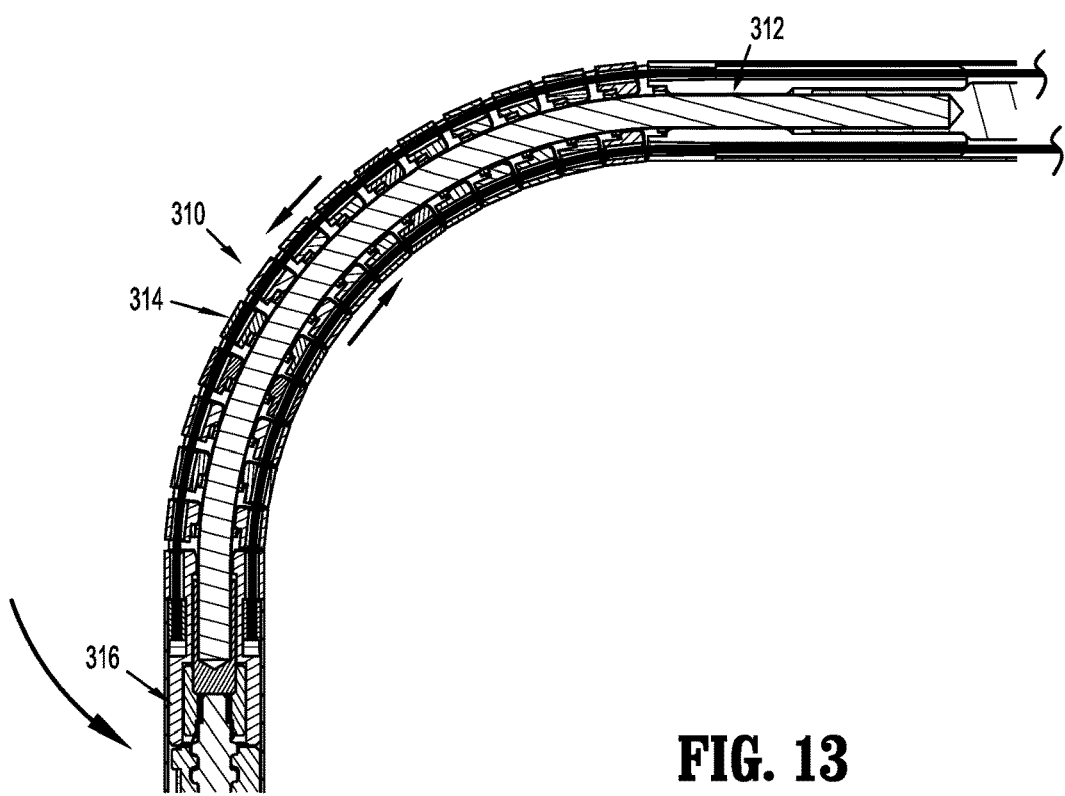
FIG. 13 is a longitudinal, cross-sectional view of the neck assembly of FIG. 9, shown in an articulated condition.

Articulation assembly 260 includes an articulation dial 262 rotatably supported in and projecting from housing 202. Articulation dial 262 is secured to or keyed to a tubular screw body 266 of articulation assembly 260. As seen in FIG. 7, articulation dial 262 includes at least one rib 262a formed on a face thereof for operative engagement with teeth 264a of a ratchet gear 264. Toothed-gear 264 functions to increase the friction for rotation of dial 262 thereby helping to maintain the position of rotation dial 264, and, in turn, the articulation of the end effector, once the user has selected a desired orientation or articulation of the end effector assembly. Additionally, toothed-gear 264 provides the user with a degree of audible/tactile feedback.

Articulation assembly 260 further includes a tubular screw body 266 rotatably supported in lumen 242c of stem portion 242b of knob 242. Tubular screw body 266 defines a central lumen 266a, through which drive shaft 250 extends, and a pair of oppositely extending helical grooves 266b, 266c formed in an outer surface thereof.

Articulation assembly 260 further includes a pair of opposed articulation cuffs 268, 270 translatably interposed between stem portion 242b of knob 242 and tubular screw body 266. Each cuff 268, 270 includes a respective rail 268a, 270a formed on an outer surface thereof and configured for slidably receipt in a respective on of the pair of opposed, longitudinally extending channels $242b_1$, $242b_2$ formed in the wall of lumen 242c. Each cuff 268, 270 further includes a respective thread portion 268b, 270b formed on an inner surface thereof and configured for slidably receipt in a respective on of the pair of oppositely extending helical grooves 266b, 266c formed in the outer surface of the tubular screw body 266. Each cuff 268, 270 is secured to a proximal end of a respective articulation cable 252, 254.

In use, as seen in FIGS. 10-14, as articulation dial 262 is rotated in a first direction, tubular screw body 266 is also rotated in the first direction. As tubular screw body 266 is rotated in the first direction, cuffs 268, 270 are caused to be translated in opposed axial directions relative to one another. As cuffs 268, 270 are caused to be translated in opposed axial directions relative to one another, so too are the respective articulation cables 252, 254 translated in opposed axial directions relative to one another. As the respective articulation cables 252, 254 are translated in opposed axial directions relative to one another, the end effector assembly is caused to be articulated off-axis. The greater the degree of rotation of articulation dial 262, the greater the degree of articulation of the end effector assembly. In order to articulate the end effector in the opposite direction, the user only needs to rotate the articulation dial 262 in an opposite direction.

Turning now to FIGS. 1-5 and 9-26, shaft assembly 300 of clip applier 100 is shown and will be described. Shaft assembly 300 and the components thereof may be formed of suitable biocompatible materials, such as, for example, stainless steel, titanium, plastics and the like.

Shaft assembly 300 includes an outer tube 302 having a proximal end 302a supported within housing 202, a distal end 302b, and a lumen 302c extending therethrough. Outer tube 302 is secured to rotation knob 242 of rotation assembly 240 by way of nubs 242d (see FIGS. 7, 15 and 30) of knob 242 extending from lumen 242c thereof and into respective openings 302d formed near proximal end 302a of outer tube 302. In use, as seen in FIGS. 14 and 15, as knob 242 is rotated, the rotation thereof is transmitted to outer tube 302 by nubs 242d of knob 242, thereby rotating shaft assembly 300 about the longitudinal "X" axis.

As seen in FIGS. 1, 2 and 9-14, shaft assembly 300 includes an articulating neck assembly 310 supported at distal end 302b of outer tube 302. Articulating neck assembly 310 permits a distal end of shaft assembly 302 to be articulated off-axis relative to the longitudinal "X" axis of clip applier 100 and of shaft assembly 300.

Articulating neck assembly 310 includes a proximal articulation joint 312 supported at and/or connected to distal end 302b of proximal outer tube 302, a plurality of inter-connected articulation joints 314 supported at and/or connected to proximal articulation joint 312, and a distal articulation joint 316 supported at and/or connected to a distal end of inter-connected articulation joints 314. Articulation cables (not shown) extend from cuffs 268, 270 of articulation assembly 260, through proximal outer tube 302, through proximal articulation joint 312, through inter-connected articulation joints 314, and are fixedly secured to distal articulation joint 316. In this manner, as articulation dial 262 is rotated, as described above, the articulation cables are translated, and thus, the neck assembly 310 is articulated.

As seen in FIGS. 16-26, shaft assembly 300 further includes an end effector assembly 320 supported at and/or connected to distal articulation joint 316 of neck assembly 310. End effector assembly 320 includes an outer tube 322 having a proximal end 322a connected to distal articulation joint 316, a distal end 322b, and a lumen 322c extending therethrough.

End effector assembly 320 further includes an upper housing 324 and a lower housing 326, each disposed within lumen 322c of outer tube 322. As seen in FIG. 16, upper housing 324 defines a window 324a formed near a distal end thereof, a longitudinally extending slot 324b formed proximal of window 324a, and a nub 324c projecting from an upper surface of upper housing 324 and located proximal of slot 324b.

As seen in FIGS. 16 and 18, end effector assembly 320 further includes a pusher bar 330 slidably disposed between outer tube 322 and upper housing 324. Pusher bar 330 includes a distal end 330a defining a pusher 330c configured and adapted to selectively engage/move (i.e., distally advance) a distal-most clip "C1" of a stack of clips "C" and to remain in contact with the distal-most clip "C1" during an initial formation thereof. Pusher bar 330 defines a distal slot 330d configured to slidably receive a tab 322b of an advancer plate 322, a proximal slot 330e located proximal of distal slot 330d and configured to slidably receive nub 324c of upper housing 324, and spring or snap clip 330f extending proximally from a proximal end 330b thereof. Snap clip 330f is configured in such a manner that the tines thereof selectively engage a nub 344d projecting from drive sled 344.

Figure 43:
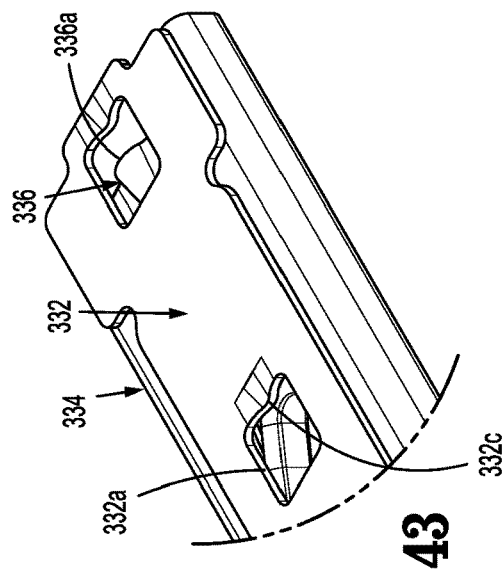
FIG. 43 is an enlarged view of the indicated area of detail of FIG. 41.
Figure 46:
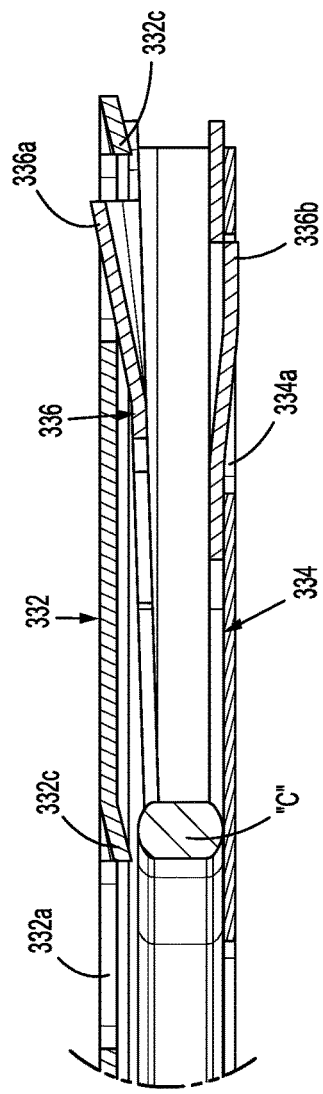
FIG. 46 is an enlarged view of the indicated area of detail of FIG. 45.

As seen in FIGS. 16 and 19, end effector assembly 320 further includes an advancer plate 332 reciprocally supported beneath upper housing 324. Advancer plate 332 includes a series of windows 332a formed therein and extending along a length thereof. As seen in FIGS. 41 and 43, each window 332a defines a proximal edge that extends below a surface of advancer plate 332 so as to define a lip or ledge 332c. Advancer plate 332 further includes a tab or fin 332b extending or projecting from an upper surface thereof, in a direction toward upper housing 324. As seen in FIG. 18, tab 332b slidably extends through slot 324b of upper housing 324 and through distal slot 330d of pusher 330.

Figure 44:
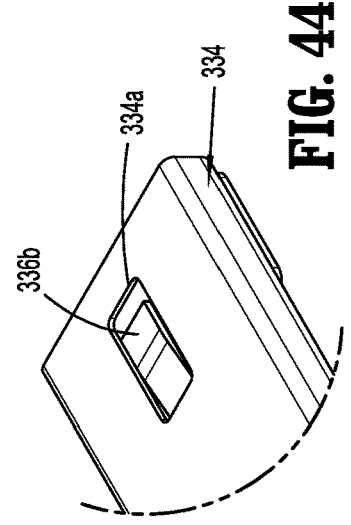
FIG. 44 is an enlarged view of the indicated area of detail of FIG. 42.
Figure 45:
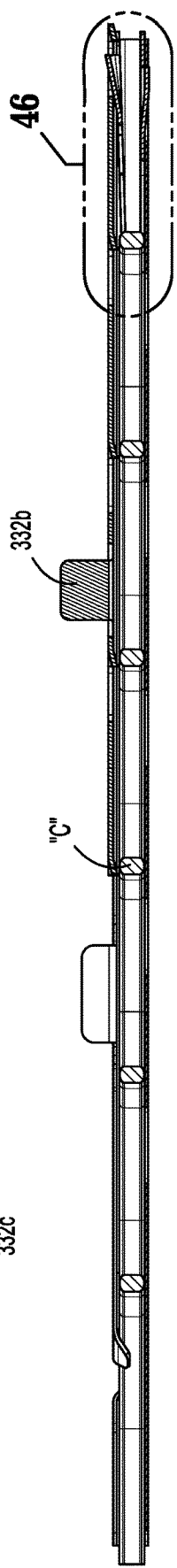
FIG. 45 is a cross-sectional view as taken through 45-45 of FIG. 41.

As seen in FIGS. 16 and 20, end effector assembly 320 further includes a clip carrier 334 disposed beneath advancer plate 332 and beneath upper housing 324. Clip carrier 334 is generally a box-like structure having an upper wall, a pair of side walls and a lower wall defining a channel therethrough. Clip carrier 334 includes a plurality of spaced apart windows 334a (see FIGS. 42 and 44) formed in the lower wall and extending longitudinally along a length thereof. Clip carrier 334 includes an elongate channel or window formed in the upper wall and extending longitudinally along a length thereof.

As seen in FIGS. 16 and 20, a stack of surgical clips "C" is loaded and/or retained within the channel of clip carrier 334 in a manner so as to slide therewithin and/or therealong. The channel of clip carrier 334 is configured and dimensioned to slidably retain the stack or plurality of surgical clips "C" in tip-to-tail fashion therewithin.

A distal end portion of clip carrier 334 includes a pair of spaced apart, resilient tangs 334b. Tangs 334b are configured and adapted to detachably engage a backspan of a distal-most surgical clip "C1" of the stack of surgical clips "C" retained within clip carrier 334.

As seen in FIGS. 16, 20 and 38-40, end effector assembly 320 of clip applier 100 further includes a clip follower 336 slidably disposed within the channel of clip carrier 334. As will be described in greater detail below, clip follower 336 is positioned behind the stack of surgical clips "C" and is provided to urge the stack of clips "C" forward during an actuation of clip applier 100. As will be described in greater detail below, clip follower 336 is actuated by the reciprocating forward and backward motion of advancer plate 332.

Figure 38:
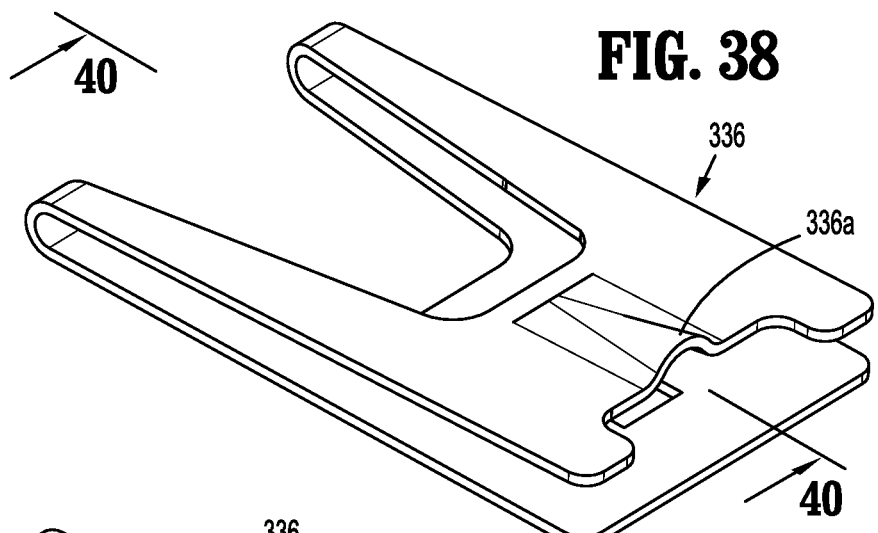
FIG. 38 is a top, perspective view of a clip follower according to the present disclosure.
Figure 39:
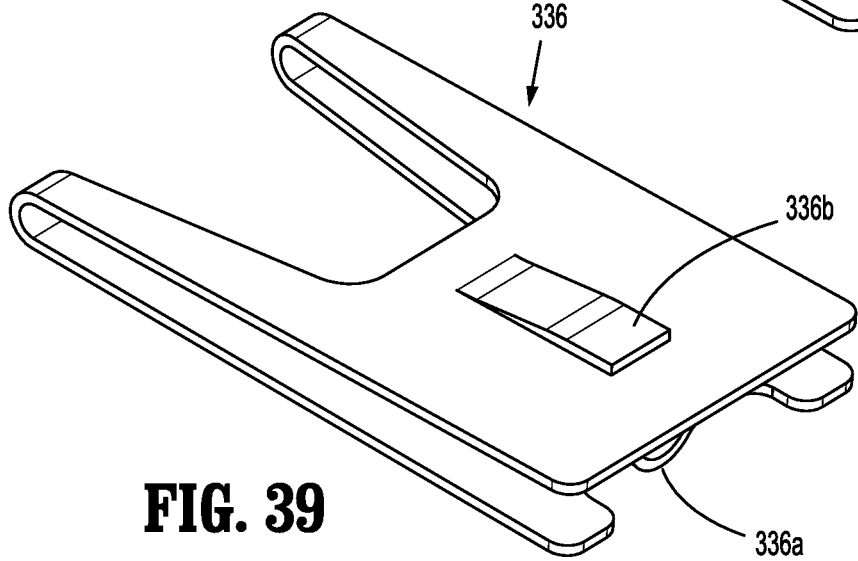
FIG. 39 is a bottom, perspective view of a clip follower according to the present disclosure.
Figure 40:
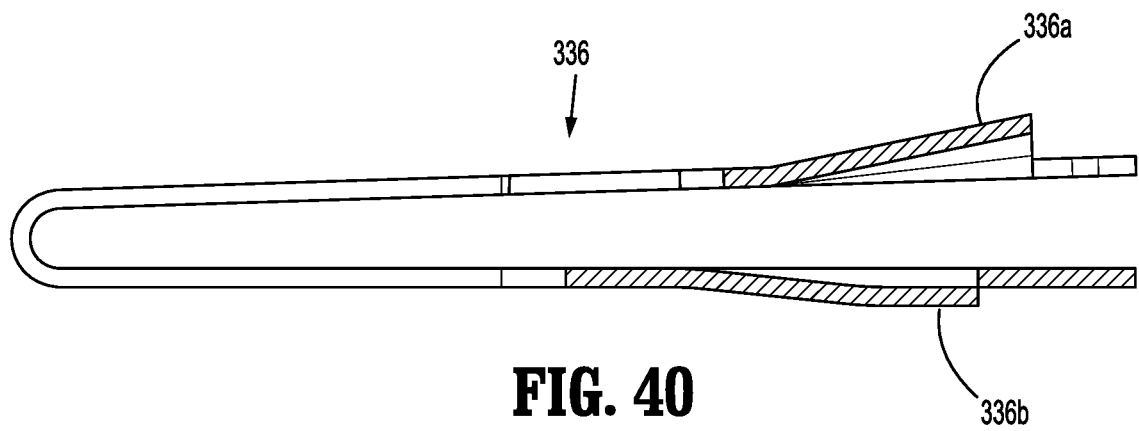
FIG. 40 is a cross-sectional view as taken through 40-40 of FIG. 38.

As seen in FIGS. 38-40, clip follower 336 includes an upper tab 336a extending substantially upwardly and rearwardly from clip follower 336, and a lower tab 336b extending substantially downwardly and rearwardly from clip follower 336.

Upper tab 336a of clip follower 336 is configured and dimensioned to selectively engage ledges 332c of windows 332a of advancer plate 332. In use, engagement of upper tab 336a of clip follower 336 against ledges 332c of windows 332a of advancer plate 332 causes clip follower 336 to incrementally advance or travel distally as advancer plate 332 is advanced or moved in a distal direction.

Lower tab 336b is configured and dimensioned to selectively engage windows 334a formed in clip carrier 334. In use, engagement of lower tab 336b of clip follower 336 in a window 334a formed clip carrier 334 prevents clip follower 336 from traveling or moving in a proximal direction.

As seen in FIGS. 16-21, end effector assembly 320 of surgical clip applier 100 includes a pair of jaws 326 mounted at a distal end of upper housing 324 and outer tube 322 and actuatable by trigger 208 of handle assembly 200. Jaws 326 are formed of a suitable biocompatible material such as, for example, stainless steel or titanium and define a channel 326a therebetween for receipt of a surgical clip "C" therein. When jaws 326 are in an open or un-approximated condition relative to each other, a width of jaws 326 measures greater than an outer diameter of shaft assembly 300. Jaws 326 are mounted in the distal end of upper housing 324 and outer tube 322 such that they are longitudinally stationary relative thereto.

As seen in FIGS. 25 and 26, each jaw 326 includes a respective raised camming surface 326b projecting from a lower surface thereof. Camming surfaces 326b of jaws 326 permit another driving camming member selective, interlocking engagement therewith, for closing and compressing of jaws 326.

As seen in FIGS. 16 and 22, end effector assembly 320 includes a driver bar 340 slidably interposed between jaws 326 and outer tube 322. Drive bar 340 defines a pair of driver camming surfaces 340a formed near a distal end thereof and being configured for selective inter-locking engagement with camming surfaces 326b of jaws 326.

End effector assembly 320 further includes a slider joint 342 connected to and extending proximally from a proximal end of drive bar 340. Slider joint 342 includes a nub 342a projecting from a surface thereof in a direction of jaws 326. Slider joint 342 includes a stem 342b extending proximally therefrom and a tab 342c projecting from a proximal end of stem 342b, in a direction away from upper housing 324.

End effector assembly 320 further includes a drive sled 344 slidably disposed within outer tube 322. Drive sled 344 includes a drive block 344a disposed proximally of upper housing 324 and defining a helical lumen 344b extending therethrough. Drive sled 344 further includes a drive channel 344c extending distally from drive block 344a, and extending between jaws 326 and outer tube 322. Drive channel 344c is configured to slidably receive tab 342c of slider joint 342 therein. Drive block 344a includes a nub 344d projecting from an upper surface thereof and being configured for selective engagement by snap clip 330f of pusher bar 330.

End effector assembly 320 further includes a helical drive screw 346 rotatably supported on upper housing 324, and extending proximally therefrom. Helical drive screw 346 is operatively connected to and/or received in helical lumen 344b of drive sled 344. A proximal end of helical drive screw 346 is connected to a distal end of a drive cable 256 (see FIG. 9) that is in turn connected to a distal end of drive shaft 250.

In use, as will be described in greater detail below, as helical drive screw 346 is rotated in a first direction, due to the rotation of drive shaft 250 and drive cable 256, helical drive screw 346 interacts with helical lumen 344b of drive sled 344 to axially advance drive sled 344, and vice-versa.

Additionally, as drive sled 344 is advanced in a distal direction, drive sled 344 pushes pusher bar 330 and is advanced distally due to the connection of snap clip 330f of pusher bar 330 with nub 344d of drive sled 344. As pusher bar 330 is advanced distally, pusher 330c thereof contacts a backspan of a distal-most clip "C1" and advances the distal-most clip "C1" in a distal direction to load the clip between jaws 326.

Also, as pusher bar 330 is advanced distally, distal slot 330d thereof is advanced distally relative to tab 332b of advancer plate 332. When tab 332b of advancer plate 332 has traversed a length of distal slot 330d, a proximal end of slot 330d abuts against tab 332b and begins to urge advancer plate 332 distally.

Concomitantly with the advancement of pusher bar 330, drive channel 334c of drive sled 344 is distally advanced and translated relative to stem 342b of slider joint 342. Drive channel 344c of drive sled 344 is advanced distally until a shoulder 344e thereof engages a shoulder 340b of drive bar 340. Drive sled 344 is configured and dimensioned such that drive sled 344 does not engage drive bar 340 until after pusher bar 330 has advanced distal-most clip "C1" into jaws 326. When shoulder 344e of drive sled 344 engages shoulder 340b of drive bar 340, drive sled 344 advances drive bar 340 in a distal direction.

Pusher bar 330 is advanced distally until proximal slot 330e thereof engages nub 324c of upper housing 324. At this point, distal advancement of pusher bar 330 is stopped. However, as helical drive screw 346 continues to rotate and advance drive sled 344 in a distal direction, nub 344d of drive sled 344 disengages from snap clip 330f of pusher bar 330 to thereby allow further distal advancement of drive sled 344.

As drive sled 344 is further advanced distally, after engagement with drive bar 340, drive bar 340 is advanced distally to thereby close jaws 326 and to form the clip "C" disposed therewithin.

As seen in FIGS. 16-26, when end effector assembly 320 is in an un-actuated condition, drive block 344a of drive sled 344 is located at a proximal end of helical drive screw 346.

Turning now to FIGS. 27-70, the operation of surgical clip applier 100, to form or crimp a surgical clip "C" around a target tissue, such as, for example, a vessel "V," will now be described. With reference to FIGS. 27-46, surgical clip applier 100 is shown prior to any operation or use thereof. As seen in FIG. 27-34, prior to use or firing of clip applier 100, trigger 208 is generally in an uncompressed or un-actuated state.

When trigger 208 is in the un-actuated position, drive block 222 is at a distal-most position on drive screw 224 of handle assembly 200. As such, pawl 234 is disposed within or is in registration with distal reversing recess 232b of toothed-rack 232.

Figure 29:
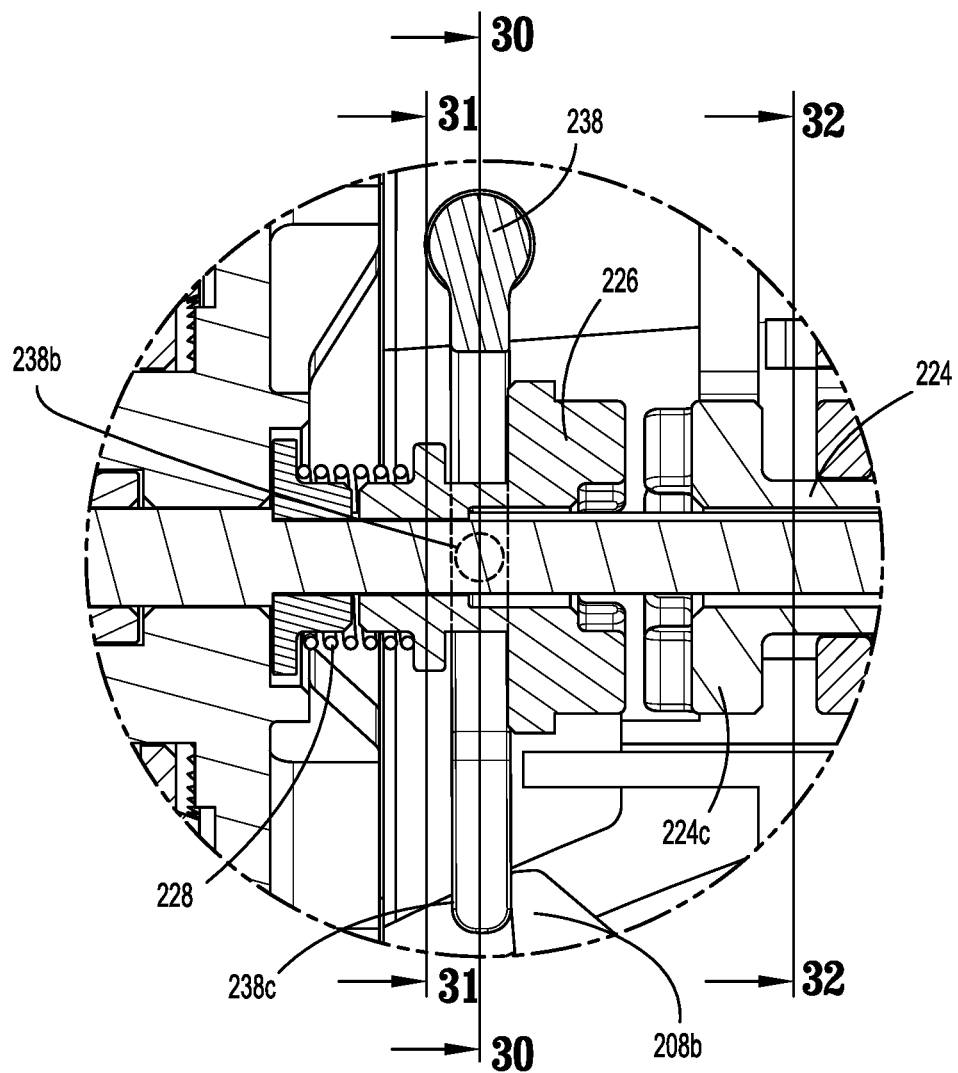
FIG. 29 is an enlarged view of the indicated area of detail of FIG. 28.
Figure 33:
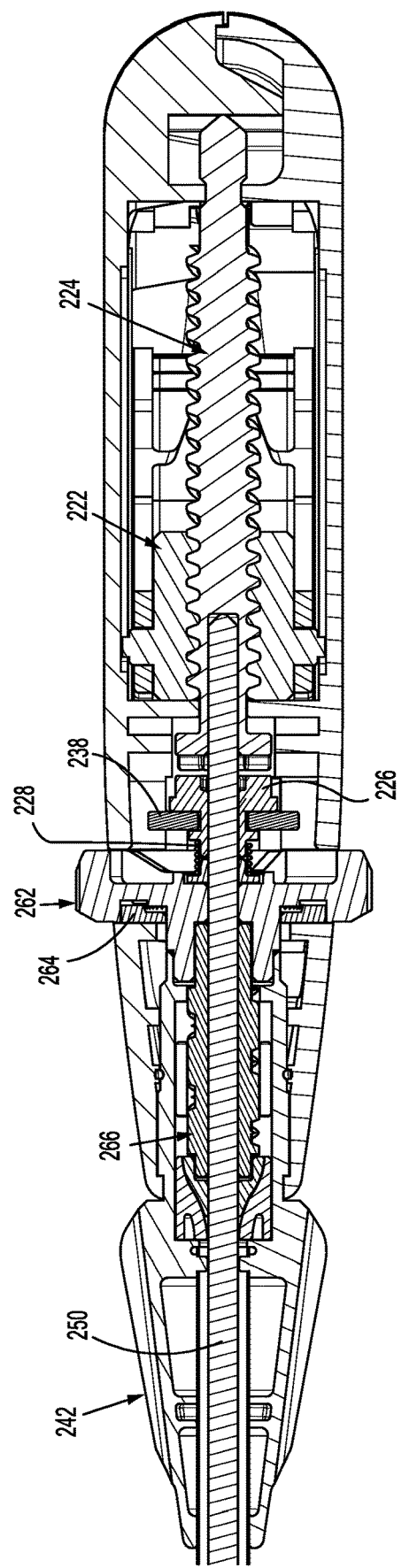
FIG. 33 is a cross-sectional view as taken through 33-33 of FIG. 28.
Figure 34:
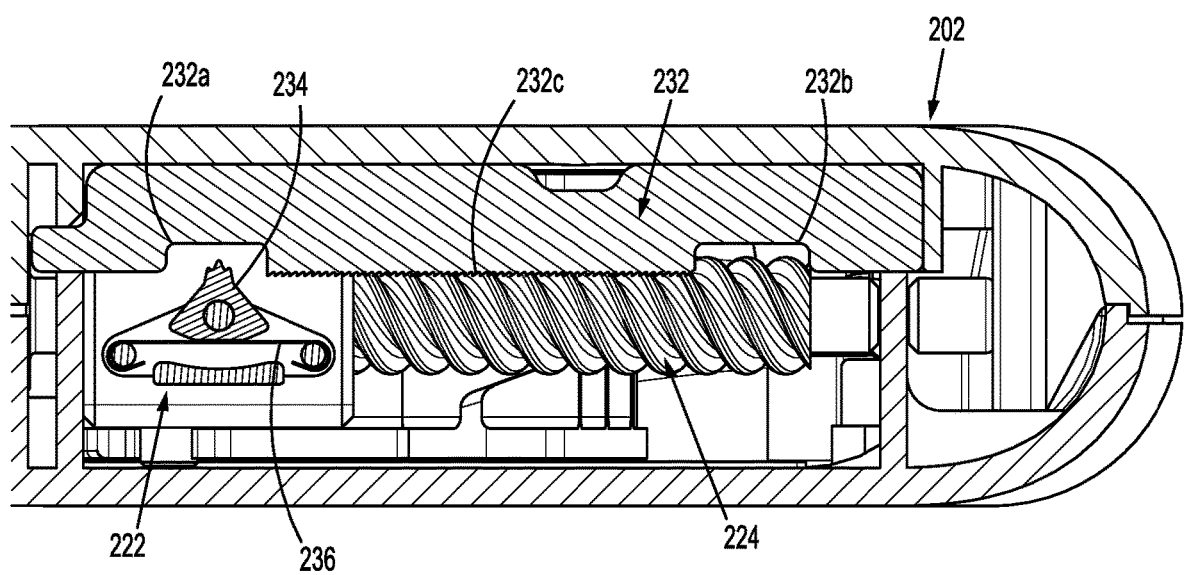
FIG. 34 is a cross-sectional view as taken through 34-34 of FIG. 28.
Figure 35:
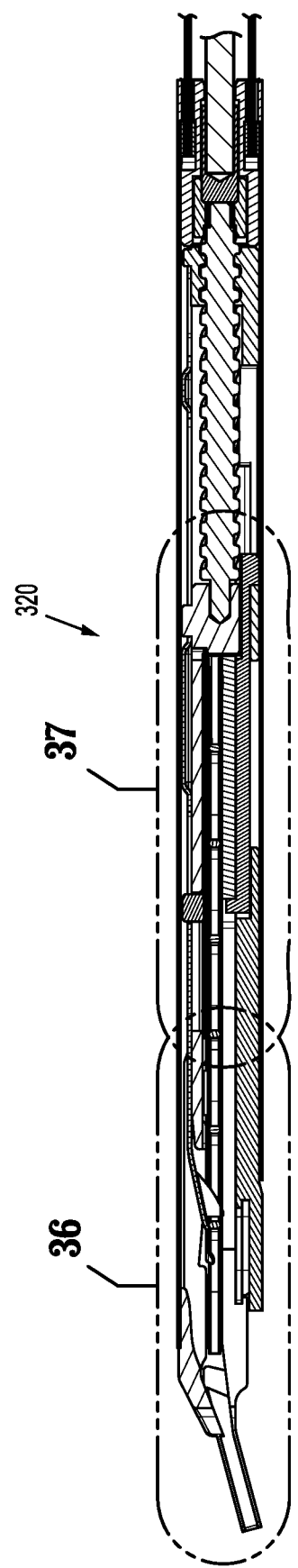
FIG. 35 is an enlarged view of the indicated area of detail of FIG. 27.
Figure 36:
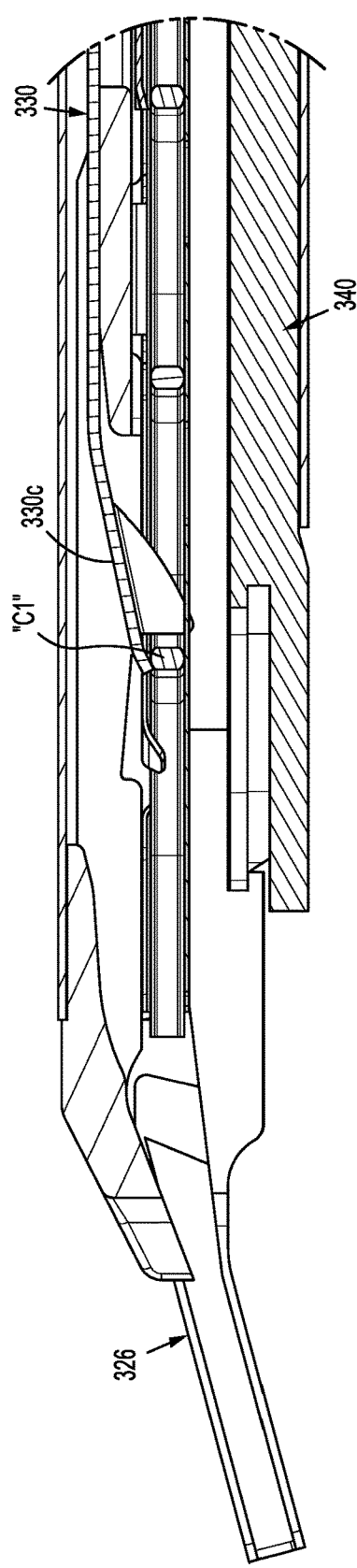
FIG. 36 is an enlarged view of the indicated area of detail of FIG. 35.
Figure 37:
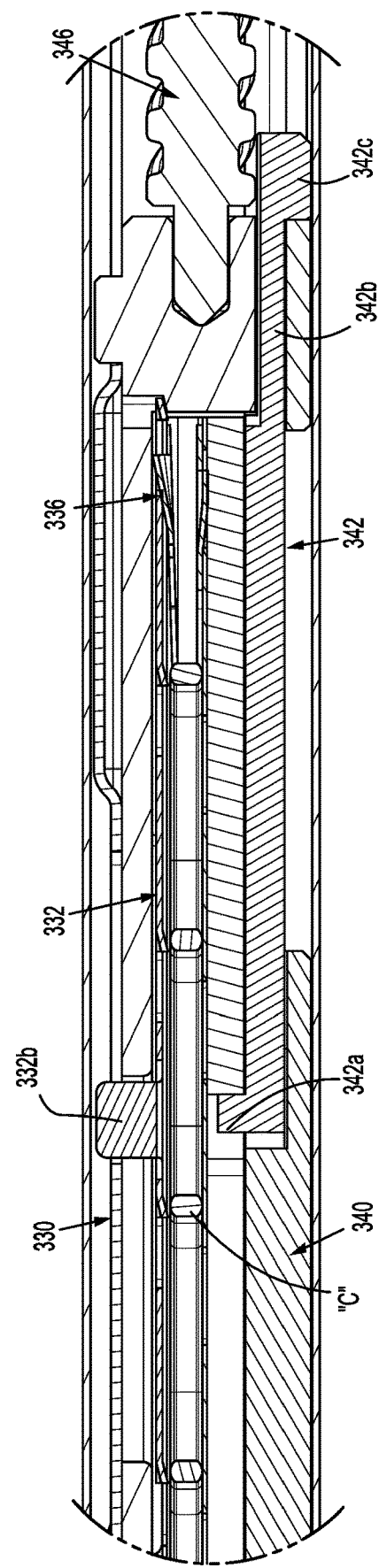
FIG. 37 is an enlarged view of the indicated area of detail of FIG. 35.

With trigger 208 in the un-actuated position, as seen in FIG. 29, rib 208b of trigger 208 contacts free end 238c of clutch bracket 238 and urges clutch bracket 238 in a distal direction to thereby maintain clutch gear 226 separate from the crown of teeth of 224c of drive screw 224.

As seen in FIGS. 35-46, with trigger 208 in the un-actuated position, pusher bar 330 is at a proximal-most position such that pusher 303c thereof is disposed proximally of the backspan of a distal-most clip "C1" of the stack of clips. Also, drive sled 344 is disposed at a proximal-most position on drive screw 346 of end effector assembly 320.

Figure 47:
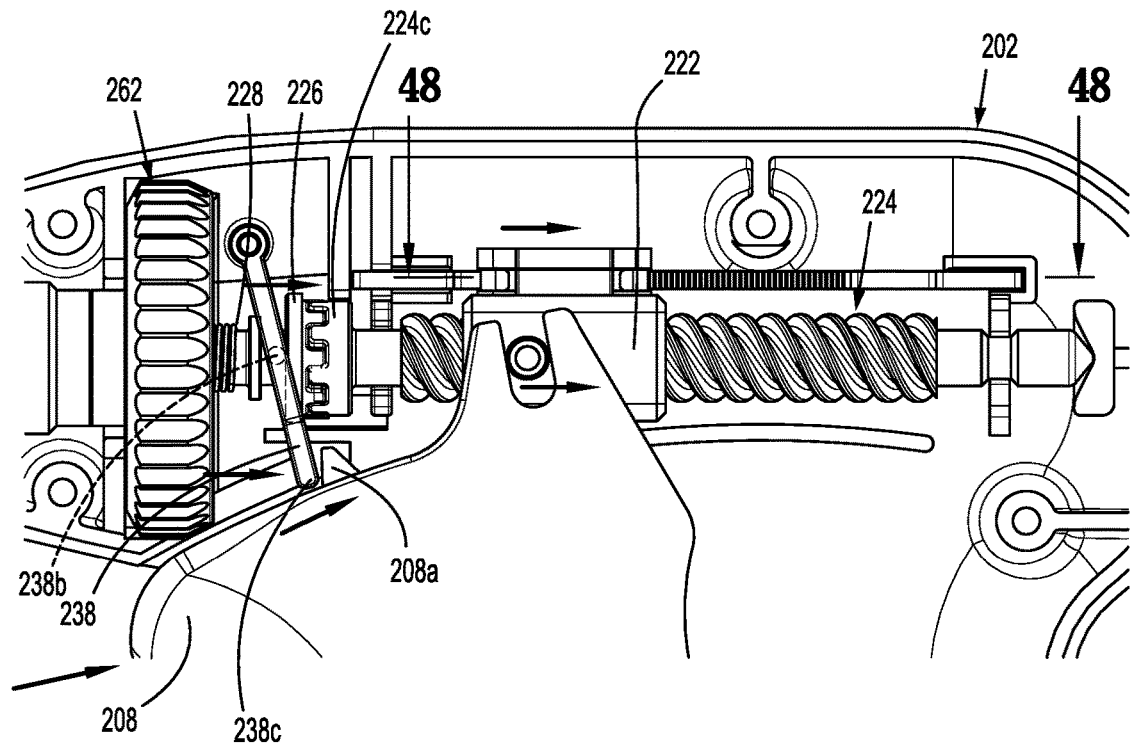
FIG. 47 is a right side, elevational view of the internal components of the handle assembly, illustrating an initial actuation of the trigger of the surgical clip applier.
Figure 48:
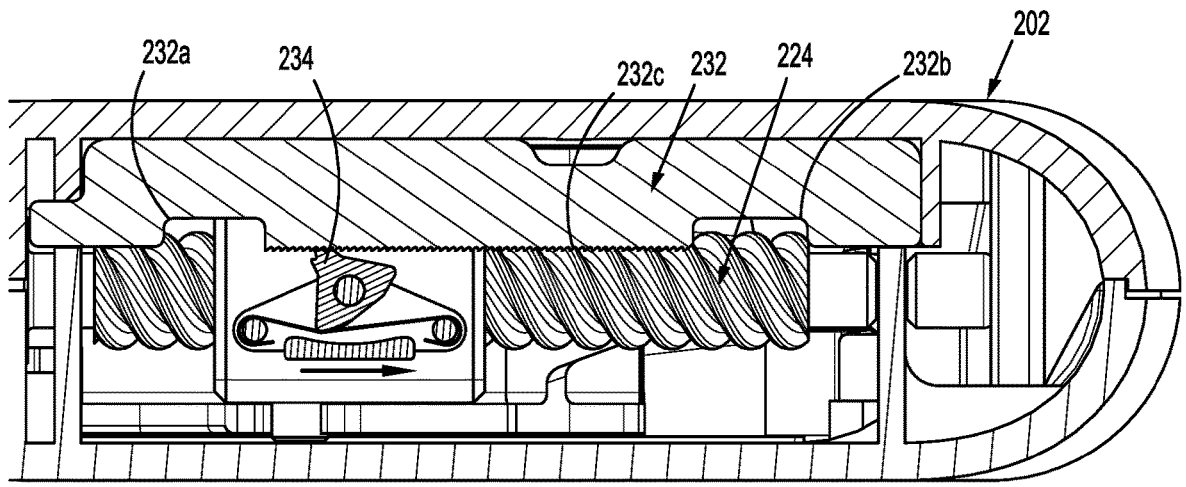
FIG. 48 is a cross-sectional view as taken through 48-48 of FIG. 47.
Figure 51:
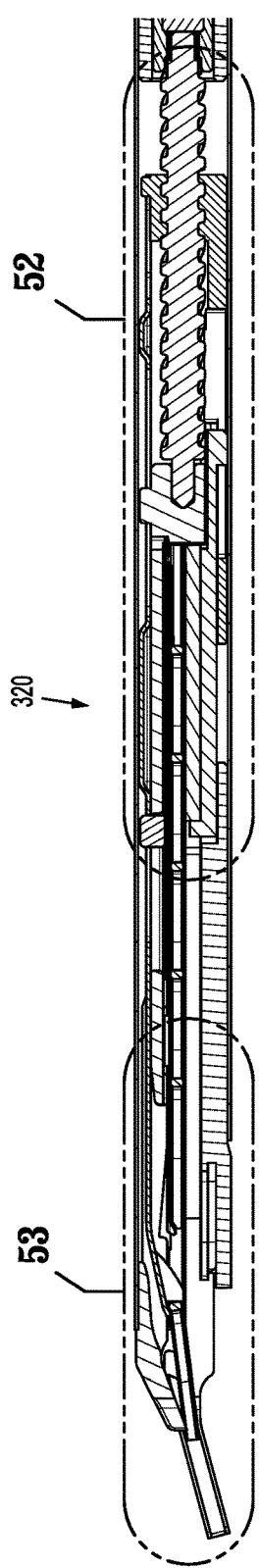
FIG. 51 is a cross-sectional view as taken through 51-51 of FIG. 49.

Turning now to FIGS. 47 and 48, during an initial actuation or firing of trigger 208, trigger 208 acts on drive block 222 to urge drive block 222 in a proximal direction. As drive block 222 is moved in the proximal direction, drive block 222 acts on drive screw 224 of handle assembly 200 to cause drive screw 224 to rotate. Additionally, as drive block 222 is moved in the proximal direction, pawl 234 is moved from distal reversing recess 232b of toothed-rack 232 to the teeth 232a of toothed-rack 232. In this manner, trigger 208 can not return to an un-actuated position until a complete stroke thereof is achieved.

As trigger 208 is initially actuated, rib 208b of trigger 208 is moved from contact with free end 238c of clutch bracket 238 allowing biasing member 228 to urge clutch gear 226 into operative engagement with the crown of teeth of 224c of drive screw 224 and thus cause clutch bracket 238 to pivot. With clutch gear 226 into operative engagement with the crown of teeth of 224c of drive screw 224, rotation of drive screw 224 of handle assembly 200 results in rotation of drive shaft 250, and in turn drive screw 346 of end effector assembly 320.

As seen in FIGS. 49-53, during the initial actuation of trigger 208, as drive screw 346 of end effector assembly 320 is rotated, drive screw 346 interacts with helical lumen 344b of drive sled 344 to axially advance drive sled 344. As drive sled 344 is advanced in a distal direction, drive sled 344 pushes pusher bar 330 and is advanced distally due to the connection of snap clip 330f of pusher bar 330 with nub 344d of drive sled 344. As pusher bar 330 is advanced distally, pusher 330c thereof contacts a backspan of a distal-most clip "C1" and advances the distal-most clip "C1" in a distal direction to move distal-most clip "C1" beyond tangs 334b of clip carrier 334 and to load the distal-most clip "C1" between jaws 326.

Figure 52:
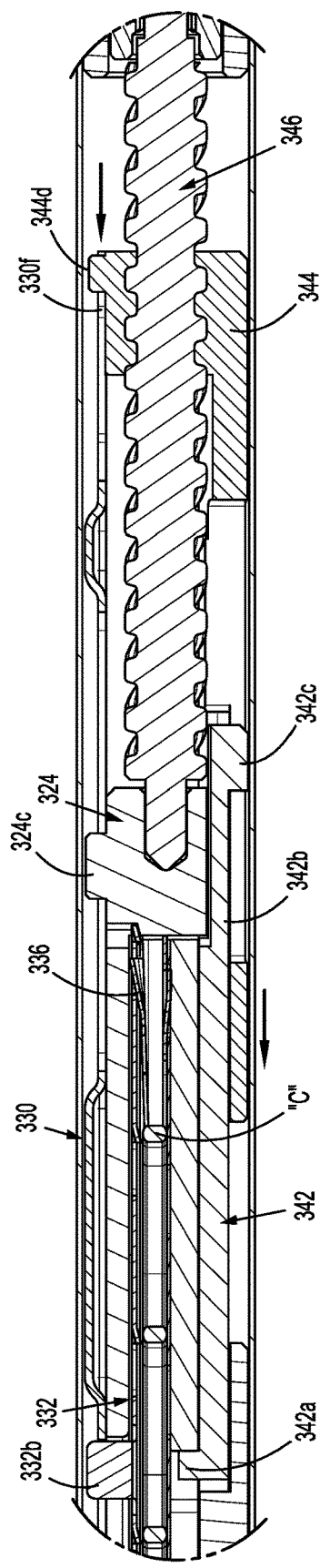
FIG. 52 is an enlarged view of the indicated area of detail of FIG. 51.
Figure 53:
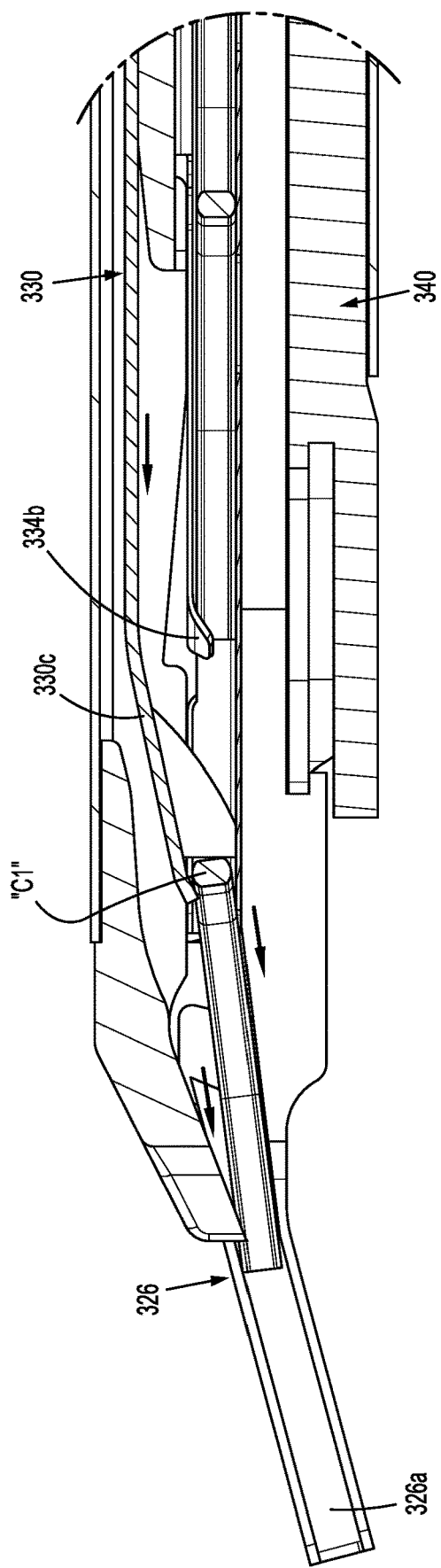
FIG. 53 is an enlarged view of the indicated area of detail of FIG. 51.
Figure 54:
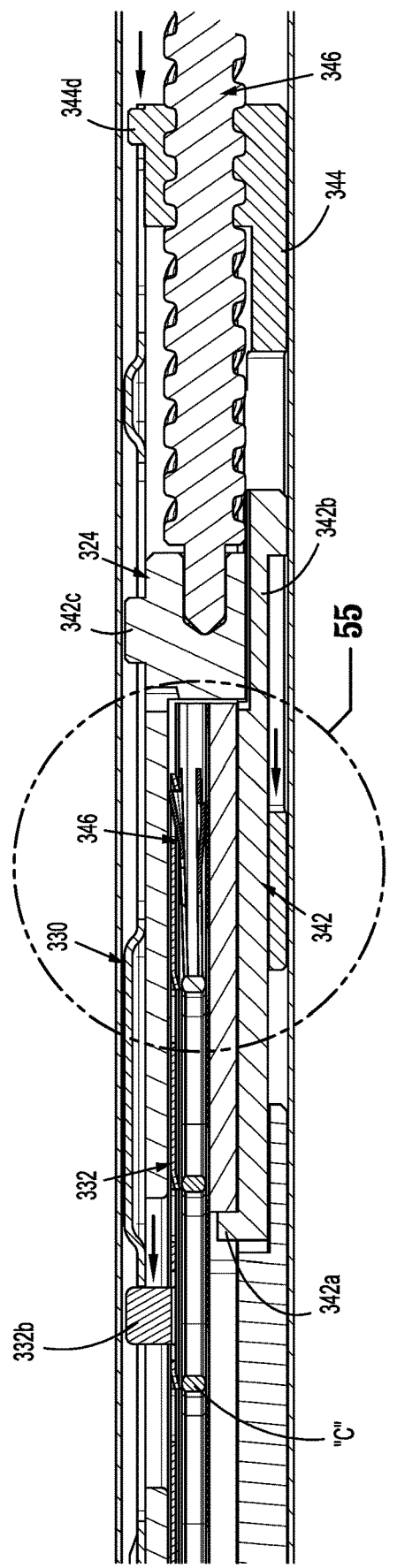
FIG. 54 is an enlarged, cross-sectional view of the area indicated as 52 in FIG. 51, illustrating a further actuation of the trigger of the surgical clip applier.
Figure 59:
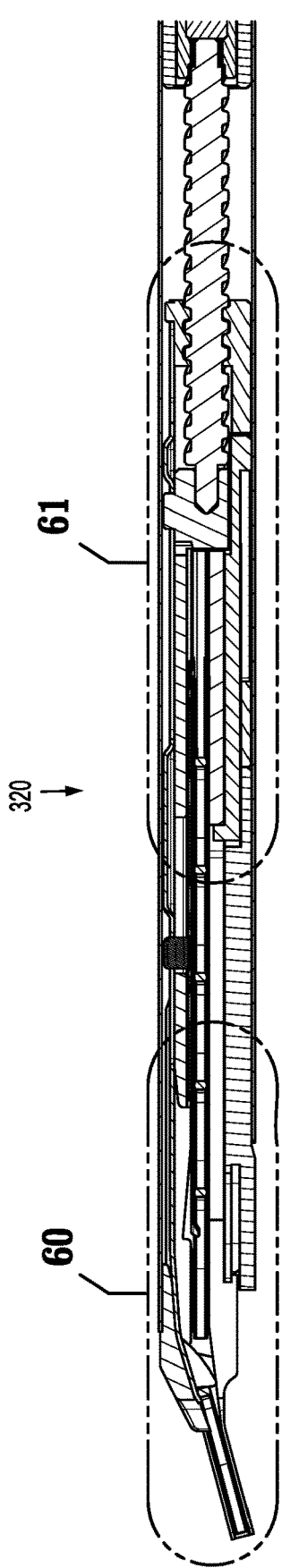
FIG. 59 is an enlarged, cross-sectional view of the area indicated as 35 in FIG. 27, illustrating the further actuation of the trigger of the surgical clip applier.
Figure 60:
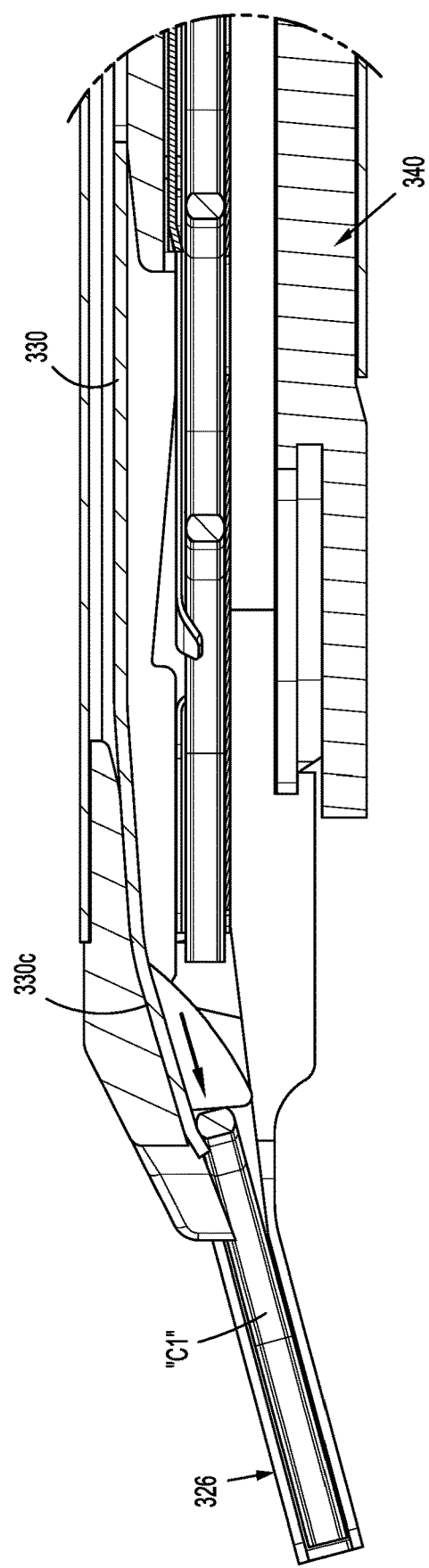
FIG. 60 is an enlarged view of the indicated area of detail of FIG. 59.

During the initial actuation of trigger 208, pusher bar 330 is advanced distally until distal slot 330d thereof is advanced into contact with tab 332b of advancer plate 332. Also during the initial actuation of trigger 208, as seen in FIGS. 50 and 52, drive channel 344c of drive sled 344 is spaced from drive bar 340 and shoulder 344e thereof has not yet contacted drive bar 340.

Turning now to FIGS. 54-58, during a further actuation or firing of trigger 208, drive screw 224 of handle assembly 200 is continued to rotate, resulting in continued rotation of drive shaft 250, and in turn drive screw 346 of end effector assembly 320.

During the further rotation of drive screw 346 of end effector assembly 320, drive sled 344 is continued to be axially advanced. At this stage, as drive sled 344 is advanced in a distal direction, drive sled 344 continues to push pusher bar 330 distally which, in turn, pushes on tab 332b of advancer plate 332 to begin distally advancing advancer plate 332. As advancer plate 332 is advanced distally, lip 332c of advancer plate 332 engages upper tab 336a of clip follower 336 to advance clip follower 336 in a distal direction, and in turn the remaining stack o clips "C." Also, as advancer plate 332 is advanced distally, lower tab 336b thereof is pulled from a proximal window 334a of clip follower 334 and moved to an adjacent window 334a of clip follower 334.

As pusher bar 330 is further advanced distally, pusher 330c thereof continues to advance the distal-most clip "C1" into jaws 326. During the further actuation of trigger 208, pusher bar 330 is advanced distally until proximal slot 330e thereof is advanced into contact with nub 324b of upper housing 324.

Turning now to FIGS. 59-68, during a final actuation or firing of trigger 208, drive screw 224 of handle assembly 200 is continued to rotate, resulting in continued rotation of drive shaft 250, and in turn drive screw 346 of end effector assembly 320.

During the final rotation of drive screw 346 of end effector assembly 320, drive sled 344 is continued to be axially advanced. At this stage, as drive sled 344 is advanced in a distal direction, since pusher bar 330 is blocked from distal advancement by nub 324b of upper housing 324, nub 344b of drive sled 344 is disengaged from the tines of snap clip 330f of pusher bar 330 to thereby allow further distal advancement of drive sled 344.

Additionally, during the final rotation of drive screw 346 of end effector assembly 320, shoulder 344e of drive channel 344c of drive sled 344 is brought into contact with drive bar 340 and urges drive bar 340 in a distal direction. As drive bar 340 is urged in the distal direction, driver camming surfaces 340a engage camming surfaces 326b of jaws 326 to urge jaws 326 to close and form clip "C1," disposed therebetween, on a vessel "V" or the like (see FIG. 68).

Figure 63:
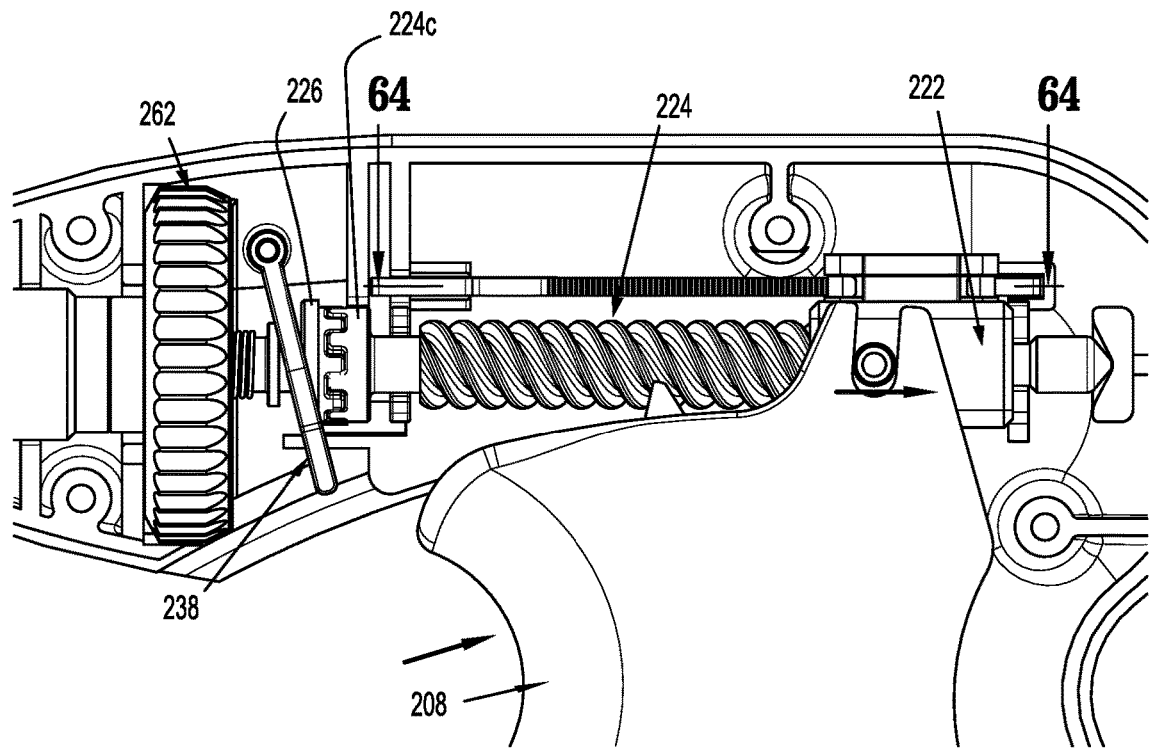
FIG. 63 is an enlarged, cross-sectional view of the area indicated as 28 in FIG. 27, illustrating a complete actuation of the trigger of the surgical clip applier.
Figure 64:
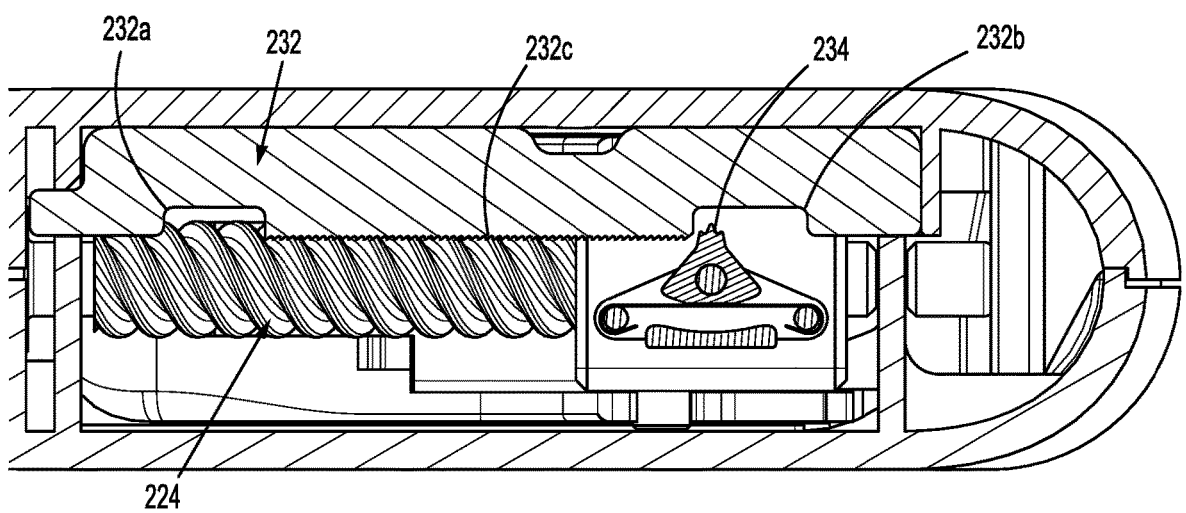
FIG. 64 is a cross-sectional view of as taken through 64-64 of FIG. 63.
Figure 65:
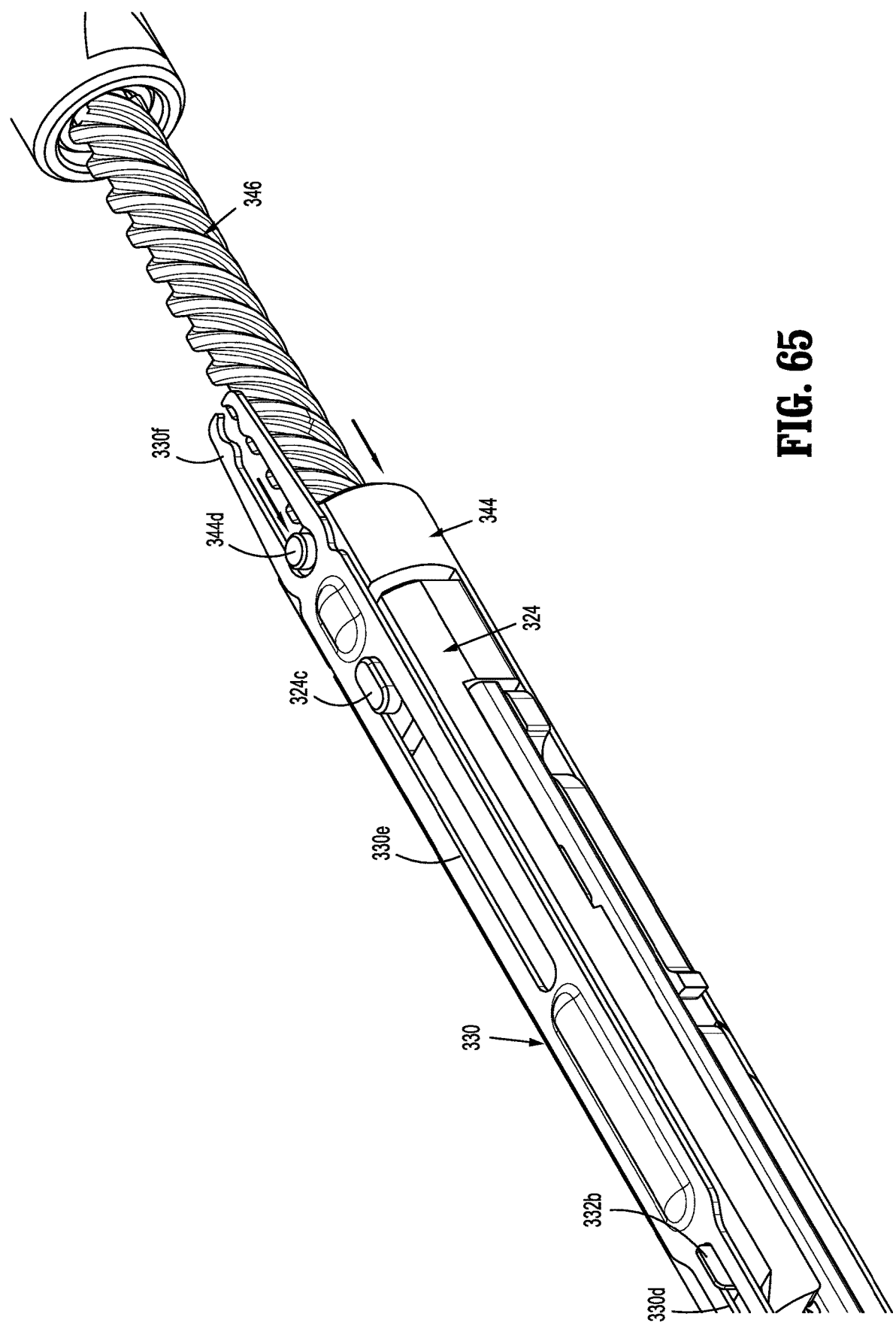
FIG. 65 is an enlarged, top, perspective view of a proximal end of the end effector assembly at the full actuation of the trigger.
Figure 66:
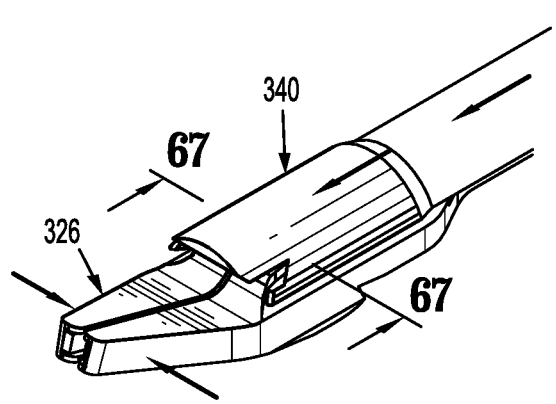
FIG. 66 is a bottom, front perspective view of a distal end of the end effector assembly, illustrating a closure of the jaws at the full actuation of the trigger.
Figure 67:
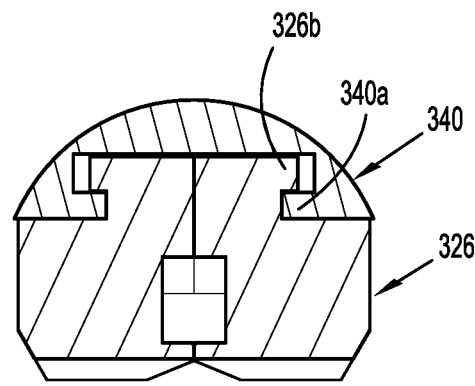
FIG. 67 is a cross-sectional view as taken through 67-67 of FIG. 66.
Figure 68:
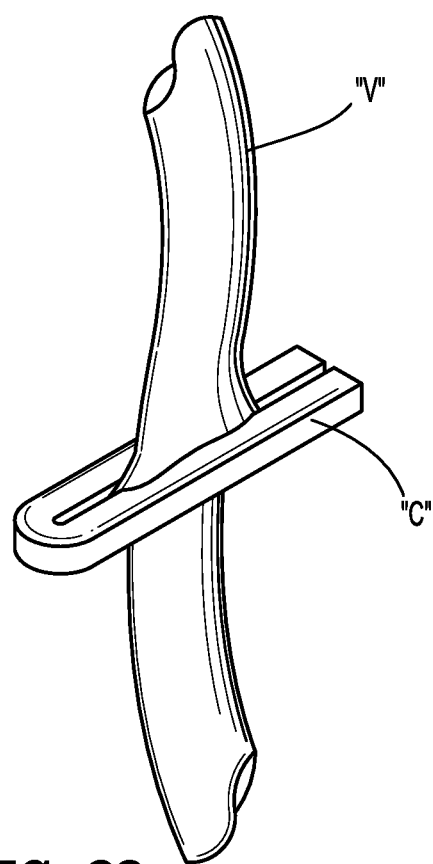
FIG. 68 is a perspective view, illustrating a surgical clip in place on a vessel.

Concomitantly therewith, as seen in FIGS. 63 and 64, as trigger 208 is fully actuated, drive block 222 is moved to a proximal-most position such that pawl 234 is moved into proximal reversing recess 232c of toothed-rack 232 wherein pawl 234 resets itself. In this manner, trigger 208 is free to return to the un-actuated position.

Figure 5:
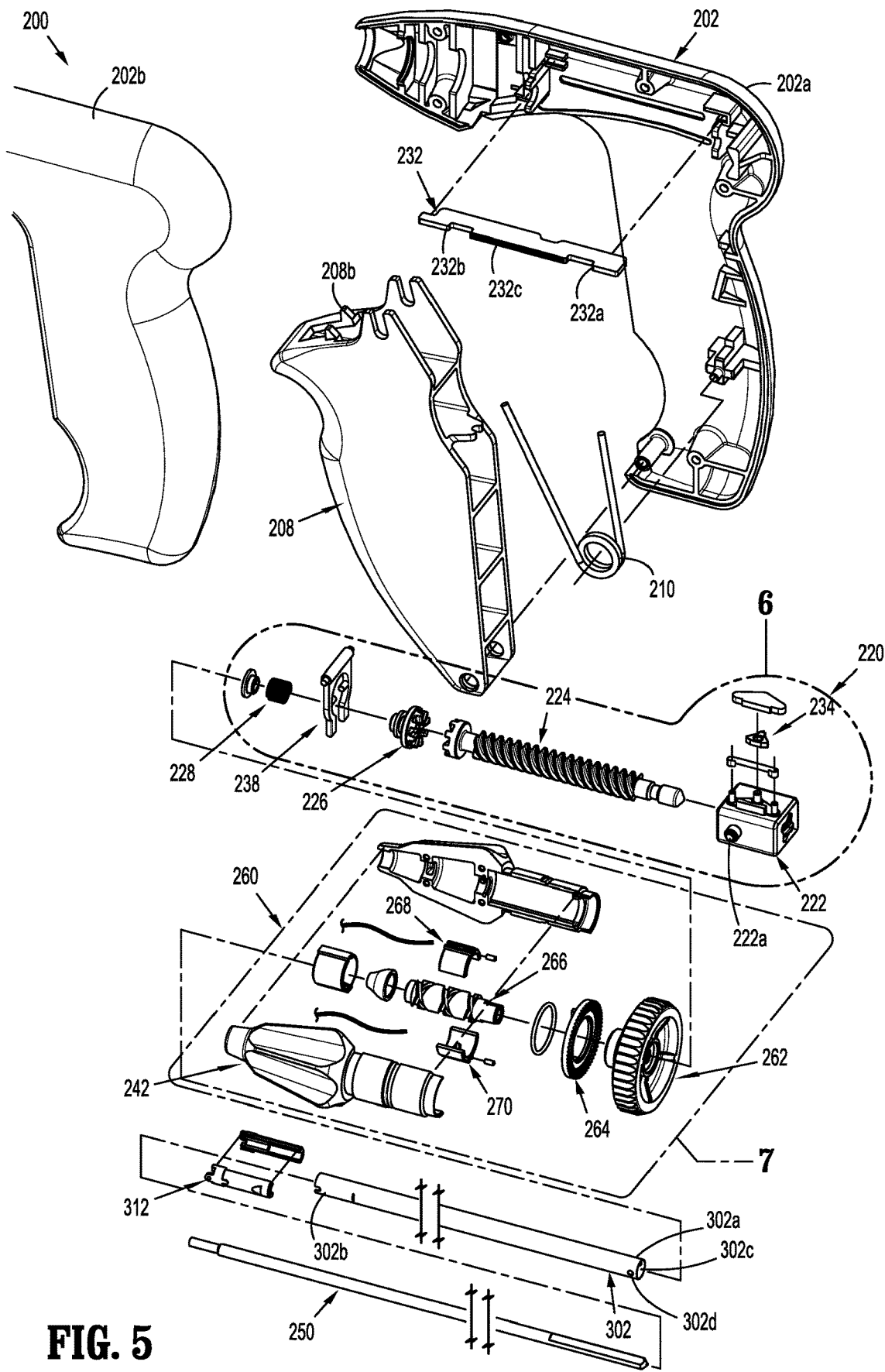
FIG. 5 is a perspective view, with parts separated, of the handle assembly of surgical the clip applier of FIGS. 1-4.
Figure 6:
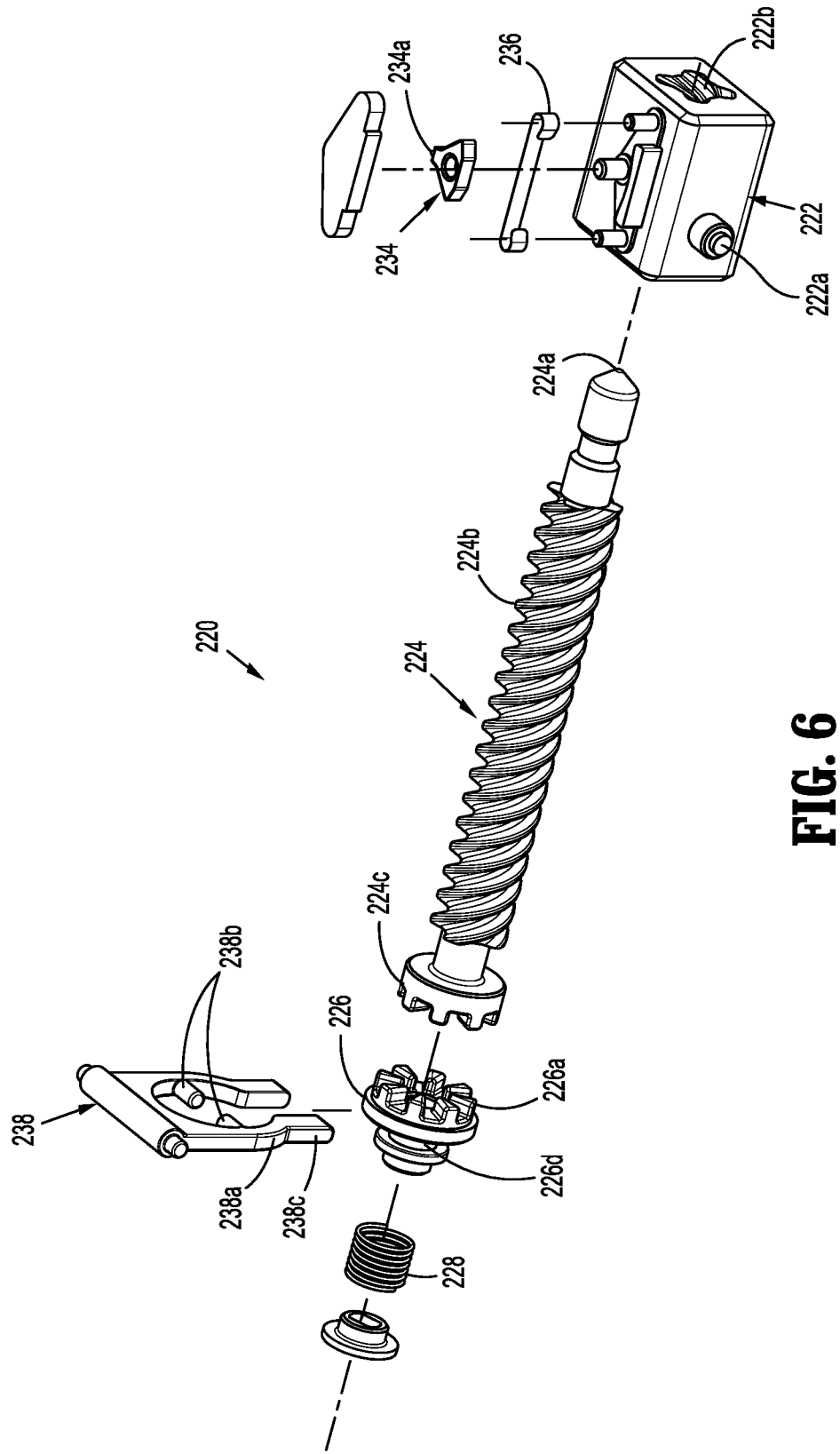
FIG. 6 is an enlarged perspective view of the indicated area of detail of FIG. 5.
Figure 69:
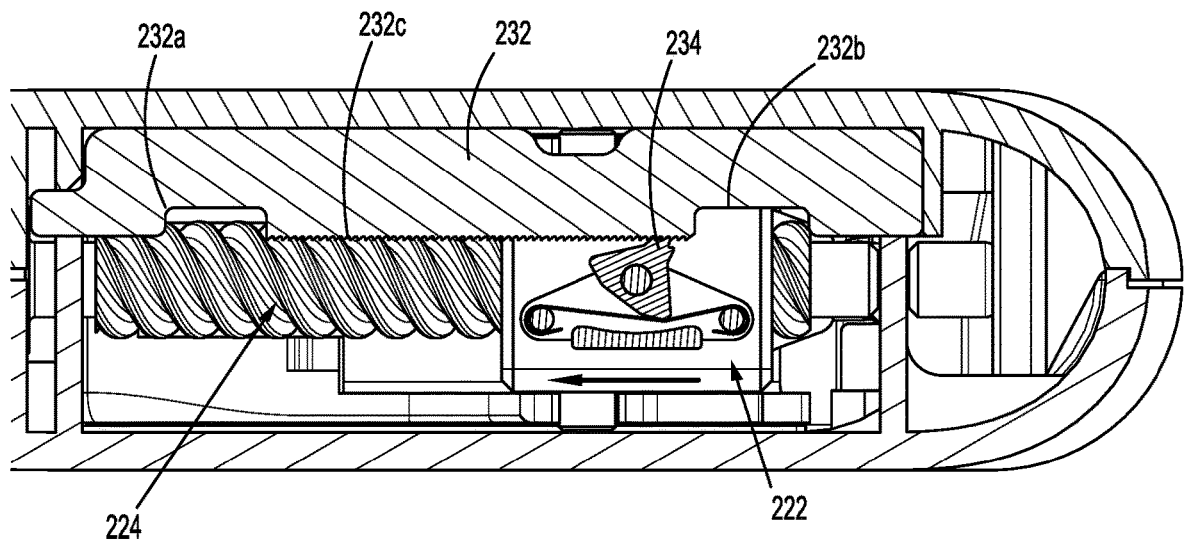
FIG. 69 is an enlarged, cross-sectional view of the area illustrated in FIG. 34, illustrating a re-setting of the trigger of the surgical clip applier.
Figure 70:
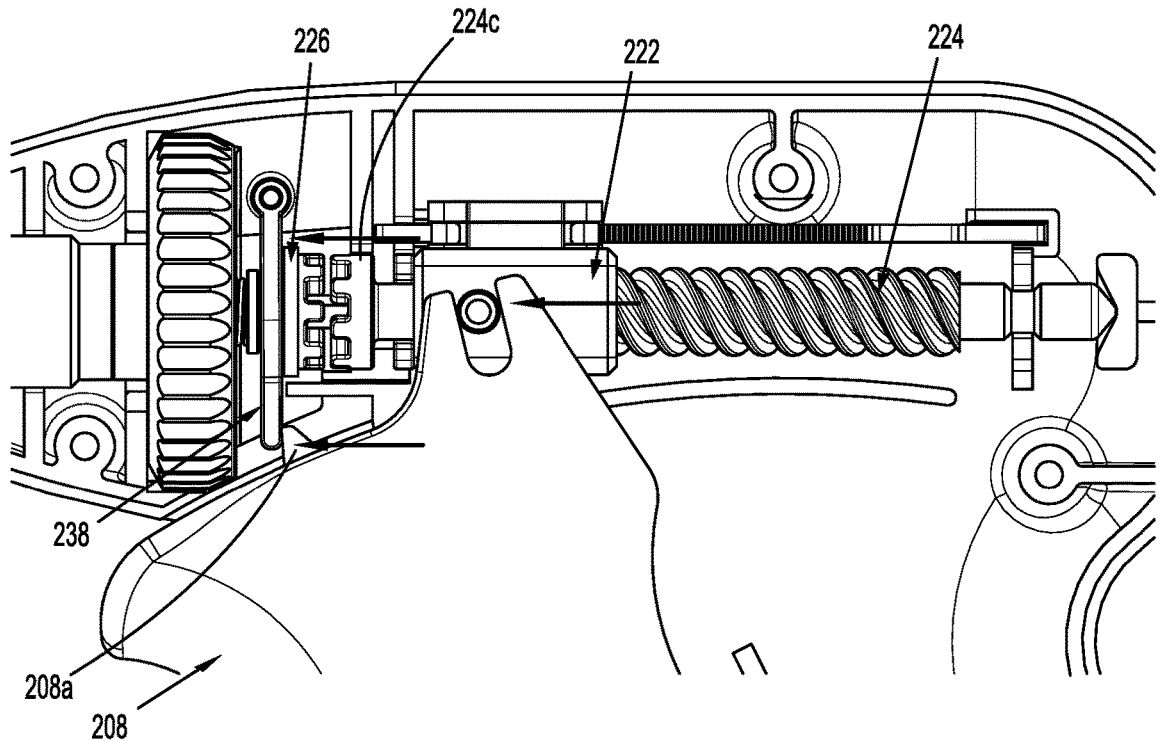
FIG. 70 in an enlarged, cross-sectional view of the area illustrated in FIG. 27, illustrating the re-setting of the trigger of the surgical clip applier.

Turning now to FIGS. 69 and 70, following a complete actuation of trigger 208 and a resetting of pawl 234, trigger 208 is released to allow trigger 208 to return to the un-actuated position due to the action of the biasing member 210 (see FIGS. 3-5). As trigger 208 is returned to the un-actuated position, trigger 208 acts on drive block 222 to urge drive block 222 in a distal direction. As drive block 222 is moved in the distal direction, drive block 222 acts on drive screw 224 of handle assembly 200 to cause drive screw 224 to rotate in an opposite direction. Additionally, as drive block 222 is moved in the distal direction, pawl 234 is moved from proximal reversing recess 232c of toothed-rack 232 ultimately to distal reversing recess 232b of toothed-rack 232.

As trigger 208 is returned to the un-actuated position, rib 208b of trigger 208 contacts free end 238c of clutch bracket 238 and urges clutch bracket 238 to disengage clutch gear 226 from the crown of teeth of 224c of drive screw 224, and to re-bias biasing member 228.

As trigger 208 is returned to the un-actuated position and drive screw 224 is rotated, drive screw 224 of handle assembly 200 reverses the rotation of drive shaft 250, and in turn drive screw 346 of end effector assembly 320. As drive screw 346 is rotated in an opposite direction following a complete actuation, drive screw 346 acts on drive sled 344 to move drive sled 344 in a proximal direction.

As drive sled 344 is moved in a proximal direction, nub 344b of drive sled 344 acts on or is re-captured by the tines of snap clip 330f of pusher bar 330 and thus pulls pusher bar 330 in a proximal direction. As pusher bar 330 is moved in a proximal direction, when a distal end of distal slot 330d thereof engages tab 332b of advancer plate 332, pusher bar 330 urges advancer plate 332 in a proximal direction until tab 332b thereof reaches a proximal end of slot 324b formed in upper housing 334. As pusher bar 330 is pulled in a proximal direction, pusher 330c thereof is caused to be moved proximal of the new distal-most clip "C1."

Additionally, as drive sled 344 is moved in a proximal direction, drive sled 334 engages tab 342c (see FIG. 16) of stem 342b of slider joint 342 to thereby pull slider joint 334 and, in turn, drive bar 340 in a proximal direction. As drive bar 340 is moved in the proximal direction, jaws 326 are allowed to re-open due to their own spring-like characteristics.

As can be appreciated, the firing sequence may be repeated as many times as desired or necessary, or until all of the clips have been fired.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
   a shaft assembly including:
      an articulating neck assembly;
      an end effector assembly supported on a distal end of the articulating neck assembly, the end effector assembly being configured to form a surgical clip in place on the body tissue, the end effector assembly including:
         a drive sled slidably axially translatable within the end effector assembly, the drive sled defining a helical lumen;
         an advancer plate slidably disposed within the end effector assembly;
         at least one clip disposed in the end effector assembly;
         jaws configured to receive and form the at least one clip;
         a pusher bar configured to load the at least one clip into the jaws, wherein the pusher bar is detachably connected to the advancer plate; and
         a drive bar configured to selectively engage the pusher bar to effectuate a closure of the jaws; and
   a rotatable drive member operatively connected to the end effector assembly, wherein a rotation of the drive member results in a loading of the at least one clip into the jaws and in a closing of the jaws,
   wherein the rotatable drive member includes an end effector drive screw threadably engaged with the helical lumen of the drive sled,
   wherein the rotation of the rotatable drive member results in a rotation of the end effector drive screw and an axial translation of the drive sled, and
   wherein during a distal advancement of the pusher bar, the pusher bar engages the advancer plate to distally move the advancer plate.

2. The apparatus according to claim 1, wherein the drive sled is selectively engaged with the pusher bar such that a distal advancement of the drive sled results in distal advancement of the pusher bar for a given distance and then the drive sled disconnects from the pusher bar after the given distance.

3. The apparatus according to claim 1, wherein the pusher bar remains in a distally advanced position during an approximation of the jaws.

4. The apparatus according to claim 1, wherein the advancer plate includes a tab for selective engagement by the pusher bar as the pusher bar is advanced distally.

5. The apparatus according to claim 1, wherein the end effector assembly further includes a clip follower slidably supported within the end effector assembly for urging surgical clips disposed within the end effector assembly in a distal direction, the clip follower including an upper tab projecting from a first surface and a lower tab projecting from a second surface, wherein the upper tab of the clip follower engages the advancer plate as the advancer plate is moved distally such that the clip follower is moved distally to advance the surgical clips, and wherein the lower tab of the clip follower engages a feature as the advancer plate is moved proximally such that the clip follower remains stationary.

6. The apparatus according to claim 5, wherein the end effector assembly further includes a clip carrier disposed within the end effector assembly, wherein the clip carrier is configured to retain the surgical clips and the clip follower, wherein the lower tab of the clip follower engages features formed in the clip carrier.

7. The apparatus according to claim 6, wherein the clip follower is incrementally advanced through the clip carrier.

8. The apparatus according to claim 1, further comprising a housing rotatably supporting the shaft assembly, wherein the shaft assembly is rotatable about a longitudinal axis of the shaft assembly.

9. The apparatus according to claim 8, wherein the housing supports an articulation dial, wherein the articulation dial is operatively connected to the neck assembly such that actuation of the articulation dial results in articulation of the neck assembly.

10. The apparatus according to claim 9, further comprising a handle assembly supporting the shaft assembly.

11. The apparatus according to claim 10, wherein the handle assembly comprises:
    the housing;

a drive assembly;
a trigger operatively connected to the drive assembly; and
a drive block axially slidably supported in the housing, wherein the drive block is connected to the trigger and defines a helical lumen,
wherein the rotatable drive member is operatively connected to the trigger and to the end effector assembly, and
wherein actuation of the trigger results in the rotation of the drive member.

12. The apparatus according to claim 11, wherein the rotatable drive member includes:
a handle drive screw threadably engaged with the helical lumen of the drive block; and
the end effector drive screw threadably engaged with the helical lumen of the drive sled,
wherein axial translation of the drive block relative to the handle drive screw of the handle assembly results in a rotation of the handle drive screw, and
wherein the rotation of the handle drive screw results in a rotation of the end effector drive screw and the axial translation of the drive sled.

13. The apparatus according to claim 12, wherein the handle assembly includes:
an articulation screw rotatably supported in the handle assembly and being connected to the articulation dial, the articulation screw defining a pair of oppositely oriented grooves formed in a surface of the articulation screw; and
a pair of articulation actuators translatably slidably supported in the handle assembly,
wherein each articulation actuator is engaged with a respective groove of the articulation screw,
wherein a proximal end of an articulation cable is secured to a respective articulation actuator, and
wherein rotation of the articulation dial results in rotation of the articulation screw and opposed translation of the articulation actuators.

14. The apparatus according to claim 13, wherein the handle assembly further includes a ratchet operatively engaged with the articulation dial.

15. The apparatus according to claim 1, wherein the neck assembly includes a plurality of inter-connected articulation joints.

16. An apparatus for application of surgical clips to body tissue, the apparatus comprising:
a shaft assembly including:
an articulating neck assembly;
an end effector assembly supported on a distal end of the articulating neck assembly, the end effector assembly being configured to form a surgical clip in place on the body tissue, the end effector assembly including:
a drive sled slidably axially translatable within the end effector assembly, the drive sled defining a helical lumen;
at least one clip disposed in the end effector assembly;
jaws configured to receive and form the at least one clip;
a pusher bar configured to load the at least one clip into the jaws; and
a drive bar configured to selectively engage the pusher bar to effectuate a closure of the jaws; and
a rotatable drive member operatively connected to the end effector assembly, wherein a rotation of the drive member results in a loading of the at least one clip into the jaws and in a closing of the jaws,
wherein the rotatable drive member includes an end effector drive screw threadably engaged with the helical lumen of the drive sled,
wherein the drive bar is selectively engaged by the drive sled following a loading of a clip into the jaws by the pusher bar, and
wherein distal advancement of the drive sled distally advances the drive bar to effectuate the closure of the jaws.

17. The apparatus according to claim 16, further comprising a handle assembly supporting the shaft assembly.

18. The apparatus according to claim 17, wherein the handle assembly comprises:
a drive assembly;
a trigger operatively connected to the drive assembly; and
a housing and a drive block axially slidably supported in the housing, wherein the drive block is connected to the trigger and defines a helical lumen.

19. The apparatus according to claim 18, wherein the rotatable drive member is operatively connected to the trigger and to the end effector, wherein actuation of the trigger results in the rotation of the drive member.

20. The apparatus according to claim 19, wherein the rotatable drive member comprises:
a handle drive screw threadably engaged with the helical lumen of the drive block, and
the end effector drive screw threadably engaged with the helical lumen of the drive sled,
wherein axial translation of the drive block relative to the handle drive screw of the handle assembly results in a rotation of the handle drive screw, and
wherein the rotation of the handle drive screw results in a rotation of the end effector drive screw and the axial translation of the drive sled.

* * * * *